(12) United States Patent
Bandyopadhyay et al.

(10) Patent No.: US 10,321,871 B2
(45) Date of Patent: Jun. 18, 2019

(54) DETERMINING SLEEP STAGES AND SLEEP EVENTS USING SENSOR DATA

(71) Applicant: Awarables, Inc., Potomac, MD (US)

(72) Inventors: Amrit Bandyopadhyay, Washington, DC (US); Gilmer Blankenship, Washington, DC (US); Raghu Upender, Nashville, TN (US); Madhvi Upender, Potomac, MD (US); Chris Giles, Potomac, MD (US)

(73) Assignee: Awarables Inc., Baltimore, MD (US)

(*) Notice: Subject to any disclaimer, the term of this patent is extended or adjusted under 35 U.S.C. 154(b) by 0 days.

(21) Appl. No.: 15/249,108

(22) Filed: Aug. 26, 2016

(65) Prior Publication Data

US 2017/0055898 A1 Mar. 2, 2017

Related U.S. Application Data

(60) Provisional application No. 62/211,261, filed on Aug. 28, 2015.

(51) Int. Cl.
*A61B 5/08* (2006.01)
*A61B 5/00* (2006.01)
(Continued)

(52) U.S. Cl.
CPC .......... *A61B 5/4812* (2013.01); *A61B 5/0022* (2013.01); *A61B 5/0205* (2013.01);
(Continued)

(58) Field of Classification Search
CPC ... A61B 5/0476; A61B 5/4812; A61B 5/4815; A61B 5/4818
See application file for complete search history.

(56) References Cited

U.S. PATENT DOCUMENTS 4,999,772 A * 3/1991 Bowman .............. A61B 5/0205
600/484
5,259,390 A 11/1993 Maclean
(Continued)

FOREIGN PATENT DOCUMENTS

DE 102005048496 4/2007
JP 2005/152310 6/2005
(Continued)

OTHER PUBLICATIONS

International Search Report and Written Opinion in International Application No. PCT/US2016/049101, dated Nov. 25, 2016, 17 pages.
(Continued)

*Primary Examiner* — Michael J D Abreu
(74) *Attorney, Agent, or Firm* — Fish & Richardson P.C.

(57) ABSTRACT

Methods, systems, and apparatus, including computer programs encoded on a computer storage medium, for determining sleep stages and sleep events using sensor data. In some implementations, sensor data is obtained over a time period while a person is sleeping. The time period is divided into a series of intervals. Heart rate and changes in the heart rate are analyzed over the intervals. Based on the analysis of the heart rate changes, sleep stage labels are assigned to different portions of the time period. An indication of the assigned sleep stage labels is provided.

25 Claims, 14 Drawing Sheets

(51) Int. Cl.

| | |
|---|---|
| *A61B 5/024* | (2006.01) |
| *A61B 5/11* | (2006.01) |
| *A61B 5/0402* | (2006.01) |
| *A61B 5/0205* | (2006.01) |
| *A61B 5/04* | (2006.01) |
| *A61B 5/0428* | (2006.01) |
| *A61B 5/0456* | (2006.01) |
| *G16H 50/20* | (2018.01) |
| *G06F 19/00* | (2018.01) |
| *A61B 5/0476* | (2006.01) |

(52) U.S. Cl.
CPC ...... *A61B 5/02405* (2013.01); *A61B 5/02438* (2013.01); *A61B 5/0402* (2013.01); *A61B 5/04012* (2013.01); *A61B 5/0456* (2013.01); *A61B 5/04286* (2013.01); *A61B 5/0816* (2013.01); *A61B 5/11* (2013.01); *A61B 5/1118* (2013.01); *A61B 5/486* (2013.01); *A61B 5/4818* (2013.01); *A61B 5/681* (2013.01); *A61B 5/6804* (2013.01); *A61B 5/7246* (2013.01); *A61B 5/7257* (2013.01); *A61B 5/7267* (2013.01); *A61B 5/7278* (2013.01); *A61B 5/742* (2013.01); *G06F 19/00* (2013.01); *G16H 50/20* (2018.01); *A61B 5/02416* (2013.01); *A61B 5/04004* (2013.01); *A61B 5/0476* (2013.01); *A61B 5/0826* (2013.01); *A61B 5/4064* (2013.01); *A61B 5/4806* (2013.01); *A61B 5/6823* (2013.01); *A61B 5/6898* (2013.01); *A61B 2503/12* (2013.01); *A61B 2560/0242* (2013.01); *A61B 2562/0219* (2013.01); *A61B 2562/06* (2013.01)

(56) References Cited

U.S. PATENT DOCUMENTS

| | | | |
|---|---|---|---|
| 5,280,791 A | 1/1994 | Lavie | |
| 5,732,696 A | 3/1998 | Rapoport et al. | |
| 6,241,686 B1 | 6/2001 | Balkin et al. | |
| 6,878,121 B2 | 4/2005 | Krausman et al. | |
| 7,324,845 B2 | 1/2008 | Mietus et al. | |
| 2004/0073098 A1* | 4/2004 | Geva .................. | A61B 5/00 600/300 |
| 2004/0230105 A1 | 11/2004 | Geva et al. | |
| 2004/0254493 A1 | 12/2004 | Chervin et al. | |
| 2005/0115561 A1* | 6/2005 | Stahmann ............ | A61B 5/0031 128/200.24 |
| 2005/0143617 A1* | 6/2005 | Auphan .................. | A61B 5/08 600/26 |
| 2006/0060198 A1 | 3/2006 | Aylsworth et al. | |
| 2006/0111635 A1* | 5/2006 | Todros ................ | A61B 5/0402 600/484 |
| 2006/0149144 A1* | 7/2006 | Lynn .................... | A61B 5/00 600/323 |
| 2006/0235315 A1 | 10/2006 | Akselrod et al. | |
| 2007/0016095 A1 | 1/2007 | Low et al. | |
| 2007/0129769 A1 | 6/2007 | Bourget et al. | |
| 2009/0292215 A1 | 11/2009 | Todros et al. | |
| 2010/0240982 A1 | 9/2010 | Westbrook et al. | |
| 2012/0253220 A1 | 10/2012 | Rai et al. | |
| 2012/0323085 A1 | 12/2012 | Takeda | |
| 2013/0310712 A1 | 11/2013 | Kanemitsu et al. | |
| 2013/0338446 A1 | 12/2013 | Van Vugt et al. | |
| 2014/0221780 A1* | 8/2014 | Goldberger .......... | A61B 5/0402 600/301 |
| 2014/0222720 A1 | 8/2014 | Hames et al. | |
| 2015/0109124 A1 | 4/2015 | He et al. | |
| 2016/0310696 A1* | 10/2016 | Fonseca ............... | A61B 5/4812 |

FOREIGN PATENT DOCUMENTS

| | | |
|---|---|---|
| JP | 2007/195823 | 8/2007 |
| WO | WO 01/43804 | 6/2001 |
| WO | WO 02/100267 | 12/2002 |
| WO | WO 2004/026133 | 4/2004 |
| WO | WO 2006/002338 | 1/2006 |
| WO | WO 2008/132736 | 11/2008 |
| WO | WO 2009/144598 | 12/2009 |
| WO | WO 2012/112186 | 8/2012 |
| WO | WO 2012/153263 | 11/2012 |
| WO | WO 2013/054712 | 4/2013 |
| WO | WO 2015/006364 | 1/2015 |
| WO | WO 2015/103558 | 7/2015 |

OTHER PUBLICATIONS

International Search Report and Written Opinion in International Application No. PCT/US2016/049104, dated Dec. 2, 2016, 18 pages.

Cheng-Pin et al., "An RFID tag system-on-chip with wireless ECG monitoring for intelligent healthcare systems," The Effect of Applied Compressive Loading on Tissue-Engineered Cartilage Constructs Cultured With TGF-BETA3, IEEE, Jul. 2013, pp. 5489-5492.

Karlen et al., "Sleep antd Wake Classification With ECG and Respiratory Effort Signals," IEEE Transactions on Biomedical Circuits and Systems, IEEE, Apr. 2009, 3(2):71-78.

ChuDuc et al., "Effect of Calculation Algorithm on Heart Rate Variability by Chaos Theory", International Journal of Electronics and Electrical Engineering 2013, 1(3):145-148.

Krstacic et al., "The Chaos Theory and Non-linear Dynamics in Heart Rate Variability in Patients with Heart Failure", Computers n Cardiology 2008, 35:957-959.

Liang et al., "A rule-based automatic sleep staging method", Journal of Neuroscience Methods 2012, 205:169-176.

Ritterband et al., "A Behavior Change Model for Internet Interventions", Ann Behav Med. 2009, 38(1):18-27.

Stein et al., "Heart rate variability, sleep and sleep disorders", Sleep Medicine Reviews 2012, 16:47-66.

USPTO Non-Final Office Action issued in related U.S. Appl. No. 15/249,032, dated Aug. 11, 2017, 28 pages.

International Preliminary Report on Patentability, dated Mar. 15, 2018, in related International Application No. PCT/US2016/049101, 10 pages.

* cited by examiner

DETERMINING SLEEP STAGES AND SLEEP EVENTS USING SENSOR DATA

CROSS-REFERENCE TO RELATED APPLICATION

This application claims priority to U.S. Provisional Application No. 62/211,261, filed on Aug. 28, 2015. The entire contents of U.S. Provisional Application No. 62/211,261 are incorporated herein by reference.

GOVERNMENT RIGHTS

The subject matter disclosed herein was made with government support under the award/contract/grant number 1416220, awarded by the National Science Foundation. The U.S. government may have certain rights in the subject matter disclosed herein.

TECHNICAL FIELD

The present disclosure relates to systems to monitor and analyze the quality and quantity of a person's sleep.

BACKGROUND

A person's sleep can be assessed with a polysomnogram (PSG), which is a multi-channel procedure carried out in a sleep laboratory. Typically, the procedure requires labor-intensive technician support, resulting in an expensive process. The studies are typically performed for a single night in a Sleep Laboratory and sometimes also during the day to study daytime sleepiness, e.g., with a Multiple Sleep Latency Test (MSLT). The results of the sleep study are primarily (i) indices related to apnea events, such as an Apnea-Hypopnea Index (AHI), and (ii) sleep staging outputs that indicate the stages of sleep that occurred.

Sleep stages reported as a result of a sleep study often follow either the Rechtschaffen and Kales (R&K) scoring system or the American Academy of Sleep Medicine (AASM) system established in 2007. In the R&K system the stages of sleep are S1, S2, S3, S4, REM (Rapid Eye Movement), and Wake. In the AASM format, S3 and S4 were combined into a single stage, N3, with the stages of sleep being N1, N2, N3, REM, and Wake. However, a typical PSG requires multiple EEG (electroencephalogram) channels, an EOG (electrooculogram), an EKG (electrocardiogram), an EMG (electromyography), and analysis of data from other sensors. As a result, a PSG can be a rather invasive procedure and is typically administered for only a single session or two.

SUMMARY

The present application describes methods and systems for automated fusion of sensor data to determine sleep staging and sleep metrics. In some implementations, a computer-implemented method includes obtaining sensor data from biometric and environmental sensors, and using sensor fusion to predict stages of sleep, detect sleep events, determine sleep metrics and score the sleep sessions. For example, sleep stages can be determined from heart rate measurements and inertial sensors.

The techniques described in the present application can extend the benefits of sleep analysis with clinically validated mechanisms to achieve similar results as those obtained in a sleep lab in the comfort of the home environment over multiple nights. The home environment is the normal sleep environment of the subject, providing a more realistic assessment of the subject's sleep behavior. Recording over several nights permits a more accurate analysis that can be used to extract long-term sleep patterns.

The systems described herein can use a variety of techniques to analyze sleep-related sensor data and estimate sleep stages and sleep events from the data. The stages of a person's sleep can be determined using, for example, one or more of heart rate data, heart rate variability (HRV) data, and sensor data indicating motion. In some implementations, sleep stages including REM, slow wave sleep or deep sleep (N3), light sleep (N1, N2) and Wake are estimated using processes including but not limited to sensor signal pattern matching, learning, HRV frequency analysis, sensor fusion, approximate entropy detection, and/or rule-based decision making.

The processing techniques discussed herein can address several technical challenges in the implementation of a small wearable body data recorder that is not tethered to external computers. In particular, the processing techniques discussed herein allow the small, battery-operated body data recorder to produce analysis results that can effectively identify sleep stages while minimizing power consumption, network communication bandwidth, and computation while maintaining a high degree of accuracy in assigning sleep stages. At the EKG sampling rates needed for effective sleep stage determination, e.g., often between 200 Hz-2000 Hz, a significant amount of data is generated. The body data recorder may communicate with other devices over a low-power or low-bandwidth wireless connection, such as Bluetooth, which can significantly constrain the amount of data that can be reliably transmitted. The body data recorder may be designed to avoid wired connections with outside devices to avoid inconveniencing the subject, since wires connecting to other devices could potentially alter the subject's behavior and negatively affect the measurements. Further, transferring significant amounts of data is power inefficient for the battery-operated body data recorder. By performing at least the initial processing of EKG and heartbeat data locally within the wearable body data recorder, the amount of data that needs to be stored or transmitted and the amount of power consumed during transmission of data is minimized. Rather than storing or sending data for every EKG sample, the processing techniques discussed herein allow the results of beat detection, frequency analysis, and approximate entropy calculations, among others, to be stored and transmitted instead. The body data recorder may send this data further processing, e.g., by a mobile device or a remote computer system.

In some implementations, the body data recorder itself completes the processing discussed here to generate sleep stage labels. The use of a trained classifier, and the use of generated histograms as well as the other values used provide an accurate technique for determining sleep stages while also providing computational efficiency that allows the techniques to be implemented on a small, power and processing-constrained device.

In some implementations, the estimation of sleep stages is made by a sleep stage classifier that has been trained using examples of sensor data and corresponding data indicating actual sleep stages.

Methods and systems are described for classifying segments of a set of signals to a set of discrete decisions about said signals in the form of sleep stages. The method includes a procedure for training the system using an examples of input signals representing sensor measurements and corresponding data indicating actual sleep stages. The method can include evaluating a set of input signals using the trained system to predict sleep stages.

In some implementations, a computer-implemented method may use raw heart rate, smoothed heart rate, LF/HF, and approximate entropy as input signals to said system. Signals can be passed along with ground truth to the training system to generate a sleep stage evaluation engine, which can evaluate new input signals to produce a prediction of sleep stage.

In some implementations, sensor data may be obtained from a wearable device that houses sensors to capture EKG data and sensors to capture motion data such as accelerometers and gyroscopes.

In some implementations, instead of using EKG data, an estimation of heart rate is directly taken as input to the method. Both EKG data and heart rate data can be taken from sources that are worn or not in contact with the subject. For example, a sensor using cardioballistic EKG technology may be included in bedding that does not require skin contact.

In some implementations, EKG data, motion data, breathing rate data and sound data, are provided as input to the engine. In some implementations, the heart rate data may be obtained in the form of pulse-rate data from a wrist-worn device or pulse-oximeter.

In some implementations, sensor data or biometric data is obtained from polysomnography data recorded in a sleep laboratory.

In one general aspect, a method performed by one or more computing devices includes: obtaining, by the one or more computing devices, sensor data generated by one or more sensors over a time period while a person is sleeping; dividing, by the one or more computing devices, the time period into a series of intervals; analyzing, by the one or more computing devices, heart rate and the changes in the heart rate of the person indicated by the sensor data over the intervals; based on the analysis of the heart rate changes, assigning, by the one or more computing devices, sleep stage labels to different portions of the time period; and providing, by the one or more computing devices, an indication of the assigned sleep stage labels.

Other embodiments include corresponding systems, apparatus, and computer programs, configured to perform the actions of the methods, encoded on computer storage devices. A system of one or more computing devices can be so configured by virtue of software, firmware, hardware, or a combination of them installed on the system that in operation cause the system to perform the actions. One or more computer programs can be so configured by virtue having instructions that, when executed by data processing apparatus, cause the apparatus to perform the actions. Implementations can include one or more of the features discussed below In some implementations, the sleep stage labels include wake, rapid eye movement (REM) sleep, light sleep, and deep or slow-wave sleep.

In some implementations, assigning the sleep stage labels includes determining, for each of the intervals, (i) a likelihood that the interval corresponds to REM sleep, and (ii) an indication whether the interval is classified as REM sleep.

In some implementations, assigning the sleep stage labels includes determining, for each of the intervals, (i) a likelihood that the interval corresponds to light sleep, and (ii) an indication whether the interval is classified as light sleep.

In some implementations, assigning the sleep stage labels includes determining, for each of the intervals, (i) a likelihood that the interval corresponds to slow-wave sleep, and (ii) an indication whether the interval is classified as slow-wave sleep.

In some implementations, assigning the sleep stage labels includes determining, for each of the intervals, (i) a likelihood that the interval corresponds to a wake stage, and (ii) an indication whether the interval is classified as a wake stage.

In some implementations, assigning the sleep stage labels includes determining, for each of the intervals, (i) a likelihood that the interval corresponds to the person being awake or asleep, and (ii) an indication whether the person is classified as being awake or asleep.

In some implementations, the sensor data includes EKG signal data from EKG sensor.

In some implementations, analyzing the changes in the heart rate of the person includes determining heart rate variability characteristic scores for different portions of the sleep session, and the sleep stage labels are assigned based at least in part on the heart rate variability scores.

In some implementations, analyzing the changes in the heart rate of the person includes determining measures of randomness of heartbeat data for different sliding windows of the time period, wherein the sleep stage labels are assigned based at least in part on the heart rate variability scores.

In some implementations, the measure of randomness of heartbeat data is computed by determining a measure of approximate entropy based on the heartbeat data.

In some implementations, analyzing the heart rate of the person includes evaluating the value of the EKG signal in each interval with respect to the values in a neighborhood of the interval, wherein the neighborhood for each interval is a time window that extends from a first time threshold that precedes the interval to a second time threshold that follows the interval.

In some implementations, the obtained sensor data corresponds to a sleep session of the person; and analyzing the heart rate of the person includes evaluating an absolute value of the EKG signal with respect to the rest of the heart rate values for the sleep session and predetermined thresholds.

In some implementations, analyzing the changes in the heart rate of the person includes: generating a heart-rate variability (HRV) signal; performing a frequency analysis of the HRV signal; and examining a ratio of low frequency components of the HRV signal to high frequency components of the HRV signal.

In some implementations, the sensor data includes movement data from one or more motion sensors; and the method includes determining correlations of the movement data with sensor data indicating heart beats of the person, wherein the sleep stage labels are assigned based at least in part on the movement data and the correlations between the movement data and the sensor data indicating the heart beats of the person.

In some implementations, assigning a sleep stage label to a particular portion of the time period includes: obtaining likelihood scores from multiple different sleep stage analysis functions; and performing a sleep stage classification decision for the particular portion of the time period based on a combination of the likelihood scores from the multiple different sleep stage analysis functions.

In some implementations, multiple sleep stage functions and likelihoods are fused into a single sleep stage label by evaluating a classification function.

In some implementations, assigning a sleep stage label to a particular portion of the time period includes: providing multiple distinct signals that are separately correlated to sleep stages as input to a sleep stage classifier; and obtaining a single sleep stage label for the particular portion of the time period based on output of the sleep stage classifier.

In some implementations, the method includes: obtaining data sets indicating signals or function outputs, the data sets being labeled with sleep stage labels corresponding to the data sets; and training a sleep stage classifier based on the data sets to produce output indicating likelihoods that input data corresponds to a sleep stage from among a set of sleep stages.

In some implementations, the method includes: determining, for each of the signals or function outputs, a signal range histogram for the signal or function output; and using the signal range histograms to train a sleep stage classifier.

In some implementations, the method includes determining a signal range histogram for a signal, wherein the signal range histogram indicates, for each particular signal range of multiple signal ranges, a count of examples which have a particular sleep label assigned and have a value of the signal in the particular signal range.

In some implementations, determining the signal range histogram for the signal includes determining counts for each sleep label of the multiple sleep labels, for each signal range of the multiple signal ranges.

In some implementations, the method includes training or using a sleep stage classifier configured to receive, as input, signals indicating measurements during a sleep session of a person; and wherein the sleep stage classifier is configured to generate, for each interval of the sleep session, (i) a sleep stage probability distribution that indicates a likelihood for each of multiple different sleep stages, and (ii) a sleep stage label.

In some implementations, the sleep stage classifier is configured to generate the sleep stage probability distribution and the sleep stage label for a particular interval by: for each of the signals provided as input to the sleep stage classifier, accessing a histogram for the signal and determining a count indicated by the histogram for each sleep stage label corresponding to a value of the signal during the particular interval; and computing, for each of the sleep stages, a total count across all signals.

In some implementations, data used to train a sleep stage classifier and to classify sleep stage labels includes include (i) signals including data used in polysomnograms and breathing rate data, and (ii) time-correlations of sleep stages among the signals.

In some implementations, analyzing the changes in the heart rate of the person includes analyzing overlapping windows of the sensor data.

In some implementations, the sensor data includes heartbeat data from a heartbeat sensor.

In some implementations, the heartbeat sensor is an infrared sensor or an optical sensor.

In some implementations, the heartbeat sensor is a pulse rate sensor.

In some implementations, analyzing the changes in the heart rate of the person includes sampling the EKG signal at a rate between 100 Hz to 2 KHz; and applying a low pass filter to the sampled signal.

In some implementations, dividing the time period into a series of intervals includes diving the time period into adjacent periods each having a same duration.

In some implementations, dividing the time period into a series of intervals includes overlapping sliding windows having the same duration, with a sliding window being centered at each sample of heart rate data.

In some implementations, analyzing the changes in heart rate includes detecting heartbeats indicated by the sensor data.

In some implementations, detecting the heartbeats includes: detecting peaks in an EKG signal; determining a derivative signal from of the EKG signal by determining, for each sample of the EKG signal, a difference of between a current sample and the immediately previous sample; and identifying R waves based on applying one or more thresholds to the derivative signal.

In some implementations, detecting the heartbeats includes: identifying local maxima and local minima in an EKG signal; computing ranges between the maximum value of the EKG signal and minimum value of the EKG signal within each of multiple windows of the EKG signal; and assigning, to each of the multiple windows, a probability of the window representing a beat.

In some implementations, detecting heartbeats includes: evaluating data indicating a set of heartbeats determined by a heartbeat detection process; determining, based on the evaluation, a likelihood score indicating a likelihood that a beat was omitted from the detected heartbeats by the heartbeat detection process; and based on the likelihood score, missed in beat detection and labeling additional beats when computed to be likely.

In some implementations, analyzing the changes in heart rate includes determining R-R intervals for the detected heartbeats, the R-R intervals indicating an amount of time between adjacent R wave peaks in the EKG signal.

In some implementations, analyzing the changes in heart rate includes averaging the R-R intervals for beats detected within each second and then computing a measure of beats-per-minute corresponding to the average R-R interval.

In some implementations, analyzing the changes in heart rate includes determining an average heart rate for each of multiple windows of the EKG signal.

In some implementations, each of the multiple windows has a same duration, and the duration of each window is between 0.5 seconds and 5 seconds.

In some implementations, obtaining sensor data generated by one or more sensors over the time period while a person is sleeping includes obtaining sensor data for a sleep session that represents a single night.

In some implementations, obtaining the sensor data, dividing the time period into a series of intervals, and analyzing the heart rate and the changes in the heart rate are performed by a wearable, battery-operated device, wherein the wearable device includes sensors that detect the sensor data.

In some implementations, assigning the sleep stage labels and providing the indication of the assigned sleep stage labels are performed by the wearable device.

In some implementations, the method includes providing, by the wearable device, results of analyzing the heart rate and the changes in the heart rate to a second device for transmission to a server system; and wherein assigning the sleep stage labels and providing the indication of the assigned sleep stage labels are performed by the server system.

In some implementations, the second device is a mobile phone, and providing the indication of the assigned sleep stage labels includes providing, by the server system, the indication to the mobile phone for display by the mobile phone.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to limitations that solve any or all disadvantages noted in any part of this disclosure.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
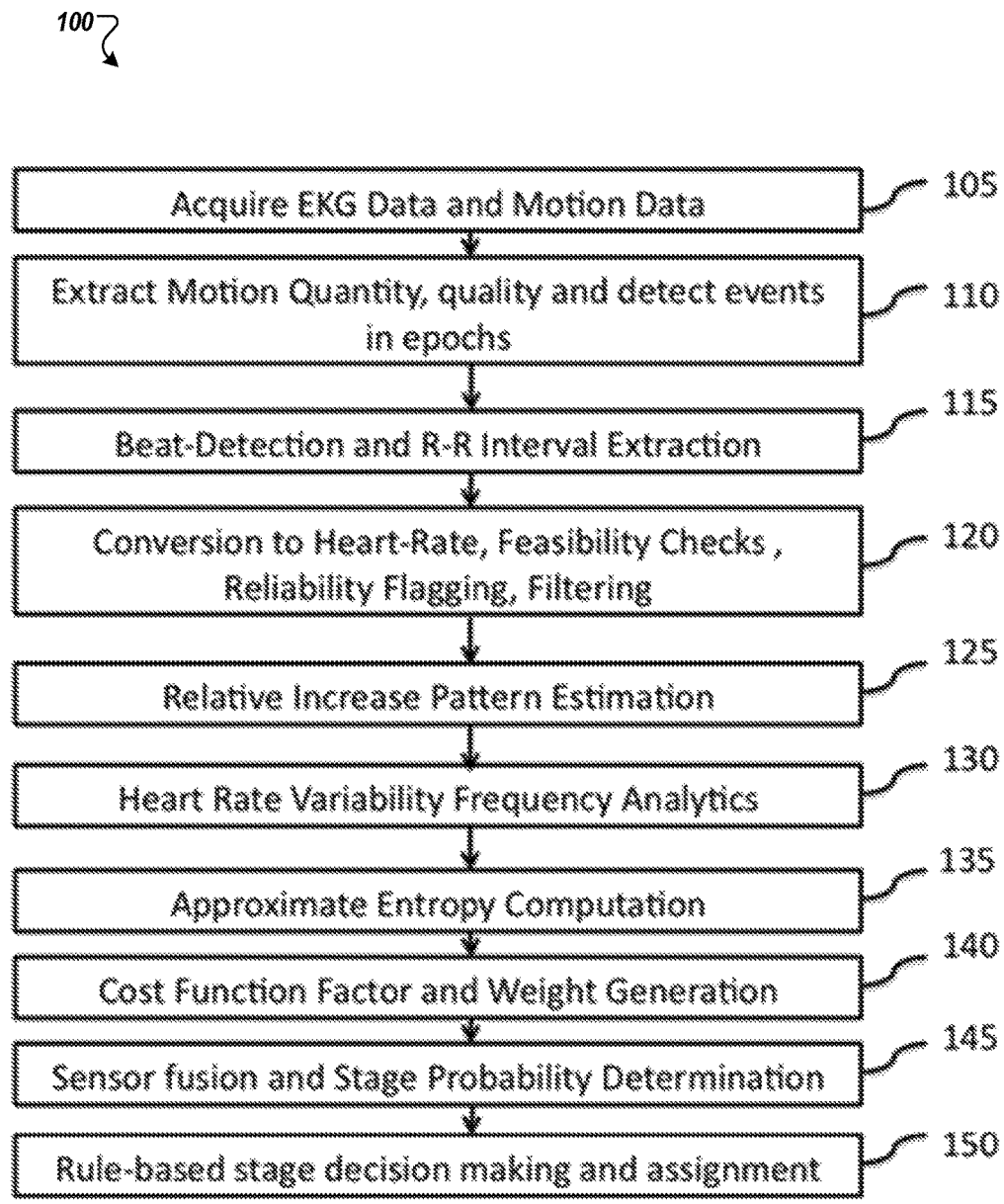
FIG. 1 is a flow diagram that illustrates an example of a method for estimating sleep stages from sensor data.

It is highly desirable to be able to extract high-accuracy sleep stage information and to compute sleep architectures for a subject in a home environment using sensors that can be housed in a comfortable, wearable device. The techniques disclosed herein allow clinically validated home sleep monitoring of this type. It would also provide an effective consumer electronic device to assess personalized health. Several sensors, including EEGs, heart rate (e.g., EKGs or PPGs—Photoplethysmograms) and heart rate variability (HRV), oxygen saturation, activity sensors, EMGs, etc., can be used to enable automatic sleep staging mechanisms. The selection and combination of sensors coupled with effective processing methods can impact the accuracy and quality of the sleep analysis and staging results. Multiple sensors can be included in a wearable device or system after taking into account their accuracy, cost, form-factor, and invasiveness.

Heart rate and heart rate variability signals can be used in a staging process closely reflecting several of the signals in the EEGs. EEGs are the key signals used for staging in sleep labs. HRV information integrates sympathetic and parasympathetic activity of the autonomic nervous system that varies across sleep stages and therefore can be an effective indicator of sleep-wake physiology.

The technology provides many different features and advantages. For example, it allows a system to take an EKG signal or heart-rate signal and determine sleep stages from it. The sleep stage detected can include REM, deep or slow wave sleep, and light sleep. The sleep stages can be determined automatically by the system, within technician scoring error for manual sleep studies. Additional aspects of heart rate can be used. For example, randomness of the heart rate signal, HRV frequency analysis, and/or approximate entropy measures can be used to determine the sleep stages. As another example, relative increases in heart rate and/or absolute value of the heart rate signal may be used by the system to classify sleep into stages. The system may also convert EKG signals to heart rate measures, which can then be further processed. The heart rate data used can be obtained from any appropriate heart-rate sensing device, pulse rate sensing device, or EKG sensing device. When EKG data is of low quality, or there are gaps or noise in the data, the techniques allow the conversion from EKG signals to heart beats and heart rate even when one or more peaks or valleys in the EKG signal are missing. The system can determine likelihoods of missed beats, and then supplement the detected beats with additional beats that were likely obscured or missing in the raw data.

Heart rate data and other data can be provided to a trained classifier that provides outputs indicative of likelihoods that the input signals correspond to different sleep stages. A sleep stage classifier can be trained to fuse different sensor signals into a single estimate. This process may train the system using any of various signals used in polysomnograms (PSGs) such as EEGs (electroencephalograms), EMGs (electromyograms), EOGs (electrooculograms), and pulse-oximetry. Other signals, such as motion data, sound data, breathing rate data, and so on can also be used as signals to the classifier. Examples of data tagged with sleep stage labels, e.g., from polysomnograms or other sources, can be used to train the classifier to estimate sleep stages from various sets of data. In some implementations, the classifier or a decision framework can learn to fuse arbitrary sets of signals and functions that are separately related to sleep into a single sleep stage prediction.

The sleep stage information allows a number of other measurements to be determined. For example, a sleep onset latency, a count of awakenings and duration of awakenings during a sleep session, and a wake time can be determined. One of the valuable results is to identify REM states and wake states. The sleep staging can be enhanced using motion sensing, especially for the detection of wake stages and REM stages.

FIG. 1 is a flow diagram that illustrates an example of a method 100 for estimating sleep stages from sensor data. The operations of the method 100 may be performed by a wearable body data recorder, such as the one described below and illustrated in FIGS. 11A and 11B. In addition, or as an alternative, the operations may be performed by another device, such as a phone or computer, that receives sensor data from the wearable device.

In step 105, EKG data for a subject is acquired while the subject is sleeping. Optionally, sensor data indicating motion of the subject can also be also be acquired. In some implementations, method 100 can take as input an EKG signal sampled at any of multiple rates. Sampling at 100 Hz to 2 KHz or more is highly effective for heart beat detection. At lower rates, beat detection is feasible with the possibility of some missed or extra beats during noisy phases in the signal. In these cases, extra processing can be used to filter out extra beats or probabilistically detect the possibility of missed beats. A signal with some noise can be filtered using a 6th order low pass Butterworth filter to remove the noise and reveal the QRS complexes.

In step 110, motion quantity and quality are determined, and events in epochs are determined. Data from one or more motion sensors, such as an accelerometer or gyroscope, can be recorded by a body data recorder. The timing of movement data can be recorded so it can be correlated with the EKG signal and/or heartbeat sensor signal detected at the same time. Other sensor data can also be detected and aligned with heart data. For example, data from a microphone, a light sensor, and other sensors can be detected and correlated with heart data for use in determining sleep stages.

In step 115, heart beats and R-R intervals are determined from the sensor data. The R-R intervals represent periods between the peaks of adjacent R waves of the EKG signal. The EKG signal can be processed by a beat detection method that examines the signal for the QRS complexes. This can be achieved using peak-detection where the R-peaks are detected above a threshold value with a minimum threshold separation in time to prevent qualification of invalid peaks. In some implementations, where the EKG source shows inversion of the signal, or signals that are biased towards the peaks, the derivative of the signal is first computed by finding the difference of every sample from the previous sample in the EKG time series. The peak detection can then be applied on this derived signal using peak and separation thresholds customized for the derivative signal.

The results of beat detection can then be used to determine the R-R intervals i.e. the time between consecutive beats. Iterating through the intervals, the heartbeat can be computed as a time-series where the heart rate for an interval of i seconds is 60/i bpm. In some implementations, the heart rate is computed every second (i.e., 1 Hz). This can be achieved by averaging the R-R intervals for beats detected within each second and then computing the beats-per-minute (bpm) corresponding to the average R-R interval. One-second time periods with no R-R intervals can be replaced with the preceding second's BPM computation.

In some implementations, where the EKG signal may have imperfections, such as missing peaks and valleys, a probabilistic method can be used for beat detection. In some implementations, overlapping slider windows can be iterated over. The slider window can be set to be the maximum distance between a peak and valley in the EKG beat signal. In each slider window, computations can be made to determine the range, max, min values. The differences of the range, max, and mins can be computed from the average range, maximum value, and minimum value in all the slider windows. These differences can be converted into probabilities that it is a peak, valley, or peak-valley range based on the statistical observations from the source. A weighted mean of the range, peak, and valley probabilities can be used to combine these individual probabilities, and to assign a probability that this window is a beat. A peak detection on these probabilities with a separation threshold, the minimum beat separation, can be used to filter out the overlapping windows.

In step 120, the beat-detection data is converted to heart rate values, and various checks or filtering can be performed. An additional iteration over all the detected beats can be performed. In this iteration, the average or median recent heart rate can be computed, and compared via a ratio to the current beat-to-beat heart rate. If the ration is very close to 0.5, it is highly likely that a beat has been missed, and a beat can be inserted at the peak or valley. Similar method can be used for sparse extra beats detected. The above method allows for detection of beats when occasionally either a peak or valley is not captured in a beat data or the entire beat is not properly captured due to device limitations.

The heart rate data, which in some implementations is computed once per second, can be checked for inconsistencies and invalid data such as outages in the heart rate stream due to any device malfunctions or incorrect beat detections. This check can be performed for all possible heart rate sources that include EKG interpretations, pulse rate recording, or heart rate reported by third-party devices. Invalid heart rate data can be detected by checking for default values that the heart rate reverts to such as zero for certain devices, and spikes and fluctuations to values that are not within the range of possible heart rate values. Invalid detection can be customized to the source EKG.

Since the nature of the heart rate signal can fluctuate substantially between different EKG or heart rate sources, a 6th order low pass Butterworth filter is used to preprocess the heart rate signal for specific subroutines in the method. In some implementations, this is implemented using a cutoff frequency of 0.01 Hz. Alternately, in some implementations, the filter is bypassed with customized filters and thresholds for different EKG or heart rate sources to account for the differences between these devices.

Figure 3:
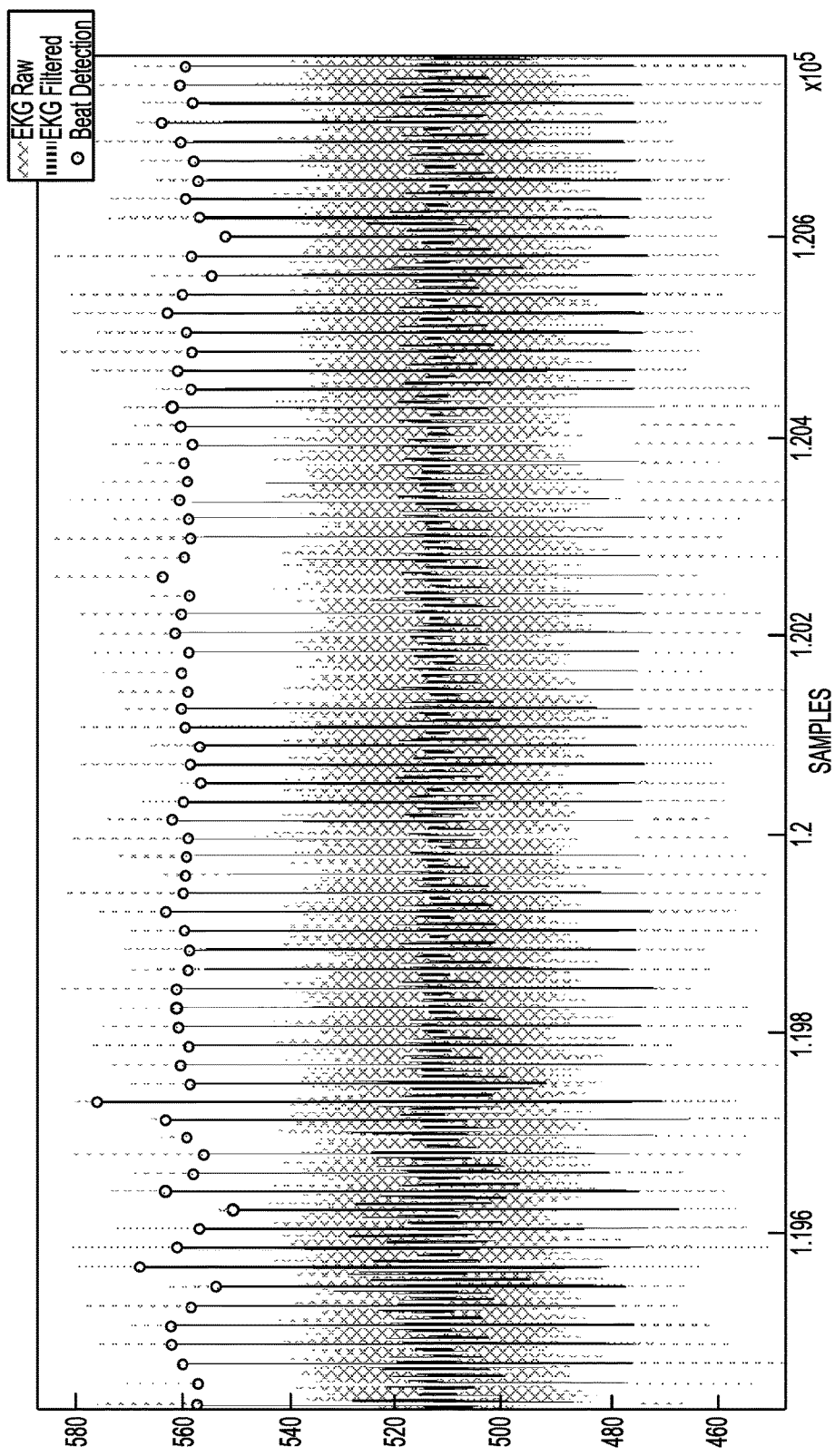
FIG. 3 is a chart illustrating an example of raw EKG data, filtered signals, and detected heart beats generated by a body data recorder (BDR) such as the one shown in FIGS. 11A and 11B.
Figure 4:
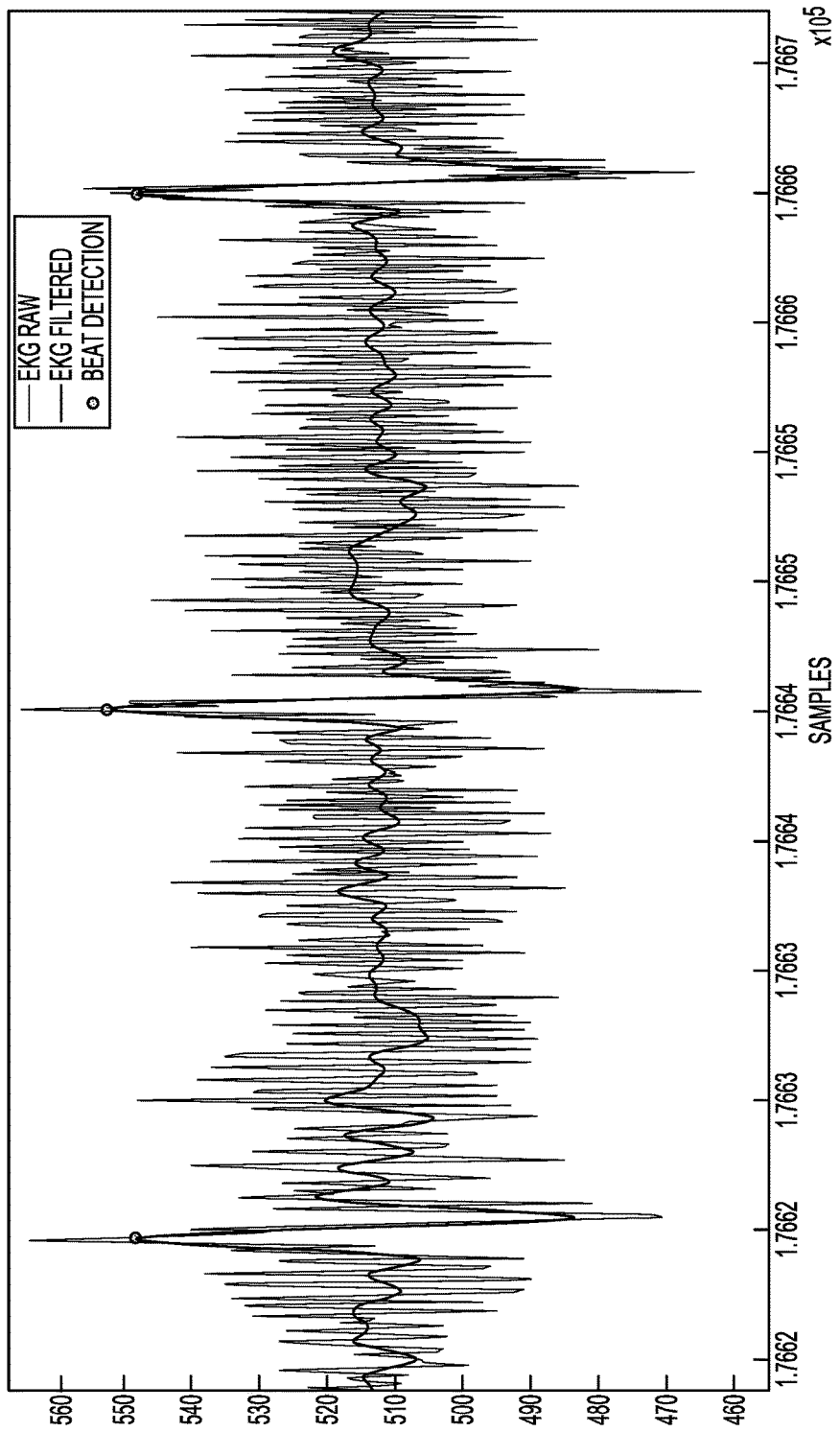
FIG. 4 is a chart illustrating a zoomed-in view of a portion of the data from the chart of FIG. 3.

FIGS. 3 and 4 illustrate examples of raw EKG data, filtered signals, and detected heart beats. Detection of the EKG data, as well as generation of the filtered signals and detected heartbeats can be performed by a wearable body data recorder (BDR) such as the one shown in FIGS. 11A and 11B. The processing techniques discussed herein allow the small, battery-operated body data recorder to produce analysis results that can effectively identify sleep stages while minimizing power consumption, network communication bandwidth, and computation while maintaining a high degree of accuracy in assigning sleep stages. At the sampling rates needed for effective sleep stage determination, e.g., often 200 Hz-2000 Hz, a significant amount of data is generated. The body data recorder may communicate with other devices over a low-power or low-bandwidth wireless connection, such as Bluetooth, which can significantly constrain the amount of data that can be reliably transmitted. The body data recorder may be designed to avoid wired connections with outside devices to avoid inconveniencing the subject, since wires connecting to other devices could potentially alter the subject's behavior and negatively affect the measurements. Further, transferring significant amounts of data is power inefficient for the battery-operated body data recorder. By performing at least the initial processing of EKG and heartbeat data locally within the wearable body data recorder, the amount of data that needs to be stored or transmitted and the amount of power consumed during transmission of data is minimized. Rather than storing or sending data for every EKG sample, the processing techniques discussed herein allow the results of beat detection, frequency analysis, and approximate entropy calculations, among others, to be stored and transmitted instead. The body data recorder may send this data further processing, e.g., by a mobile device or a remote computer system. In some implementations, the body data recorder itself completes the processing discussed here to generate sleep stage labels.

Referring again to FIG. 1, in step 125, the data is analyzed to detect relative increases in heart rate. Analysis of heart rate data reveals that an increase in heart rate is often correlated with REM and/or Wake states. These increases, especially for REM stages, can be rather subtle and the absolute value may be lower than during other stages or even the average heartbeat for the night, since the heart rate may drop through the night due to a subject's circadian rhythm. This pattern can be detected by analyzing the increase with respect to the values before and after the detected increase.

The time series can be divided into epochs to analyze the numerical trends in the data. In some implementations, the epoch size is 60 seconds. The epochs can be iterated over while calculating, for each epoch, the mean, variance, maximum value, and minimum value for heart rates in the epoch. Reference values before and after each epoch can be created by using a threshold time before and the after to analyze the neighborhood. In some implementations, this threshold is 10 minutes. The minimum of all the epoch averages in the last ten minutes before the epoch can be used to find the "previous" reference, and the minimum of all the epoch averages in the 10 minutes following the epoch can be used as the "post" reference. The number of values averaged is truncated when the epoch does not have the full time period before or after it owing to being an early or late epoch. Additionally, for the first and last epoch, the previous reference and post reference respectively, are set to the epoch's own heart rate average.

The difference of the average heart rate for the epoch and the previous reference, if positive, is used as the previous neighborhood value increase, and the differences of the average heart rate for the epoch and the post reference, if positive, is used as the post neighborhood value increase. If negative, zero is used as the neighborhood value increase. The average of these two values, i.e., post and previous deviations, is recorded as the EpochValueIncreaseEstimation.

In step 130, heart rate variability (HRV) is analyzed. In addition to the possible neighborhood increase in heart rate, REM stages have been analyzed and observed to have more "chaos" i.e., less predictability than the heart rate values in the other stages. This phenomenon can mathematically be described as tending to have higher entropy and has been investigated by the scientific community in analyses of heart health and heart failure.

Analysis of sleep data to detect disorders reveals a dramatic reduction in slow wave sleep (SWS) for patients with sleep disorders, especially those with sleep apnea, demonstrating the critical need for discriminating between light sleep (S1 or S2) and SWS sleep within NREM stages in adding value by tracking the SWS sleep quality and its improvement in subjects with sleep disorders. Heart Rate Variability can be used to extract the characteristics of this stage. Further detail about HRV analysis is discussed with respect to FIG. 2.

Figure 2:
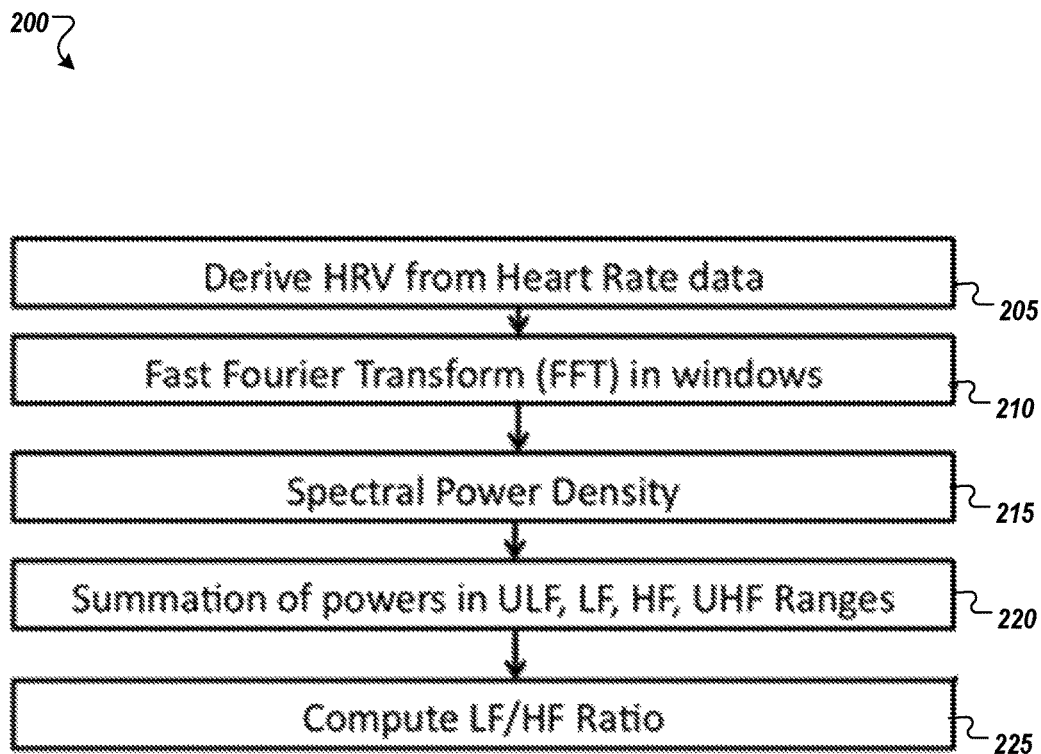
FIG. 2 is a flow diagram that illustrates an example of a method for using heart rate variability frequency analysis to determine sleep stage patterns.

FIG. 2 illustrates an example of a process 200 for using heart rate variability frequency analysis to determine sleep stage patterns. This process 200 can involve a power spectral analysis after a Fast Fourier Transform (FFT) of the HRV signal for each sleep stage can be performed. This reveals the phenomenon of SWS or deep sleep stages (S3 and S4) generally demonstrating a decrease in Low Frequency (LF) components and an increase in High Frequency (HF) components when compared to the other stages of Wake, REM, and S2. The amount of reduction and the change in the ratio of LF/HF (where LF is the summation of the powers in the LF range, and HF is the summation of the powers in the HF range) was found to vary from subject to subject. This phenomenon is due to the increased vagal activity during SWS stages and the activation of the parasympathetic nervous system (PSNS) over the sympathetic nervous system (SNS) during other stages. This can also be identified as the cardio-pulmonary-coupling (CPC). Incidentally, the lack of this type of activity has been noted in post-myocardial infarction patients.

In step 205, HRV is derived from heart rate data. For the HRV frequency analysis, the HRV is first computed for the heart rate time series as the difference between heart rates at to adjacent periods, e.g., HRV(i)=HR(i)−HR(i−1), resulting in a HRV time series of length N−1 for a heart rate time series of length N at a sampling rate of $f_s$.

In step 210, a Fast Fourier Transform (FFT) is performed on windows of the data. The time series can again be divided into sub-windows and in each window the time domain HRV can be converted to the frequency domain representation using an N-point FFT where Y=fft(window HRV,N). In some implementations the window size is 5 minutes. The value of N in the embodiment is the number of HRV samples in this time window.

In step 215, a power spectral density measurement is determined. The power spectral density, e.g., a measurement of the energy at various frequencies, can be computed using the complex conjugate, where $P_{yy}=(Y \times \overline{Y})/N$ represents the power computed at certain frequencies, $f=f_s/N[0, 1, \ldots, N-1]$. In some implementations, the power is computed at 300 frequencies, i.e. the window size, evenly spaced between 0 and 1 Hz In step 220, power measurements are summed over certain frequency ranges. For example, two ranges may be defined, with one range defined as a low-frequency or LF Range, and another range defined as a high-frequency or HF Range. In some implementations the LF Range is 0.04-0.15 Hz, and the HF Range is defined as 0.15-0.4 Hz. The LF Power can be computed by summing the powers in the power spectral density for the frequencies that lie in the LF Range (i.e. the corresponding elements in $P_{yy}$ for the range of frequency elements in f). The HF Power can similarly be computed for the HF Range. For each window the LF/HF, and LF % i.e., LF/(LF+HF) can be computed.

In step 225, the LF/HF Ratio is computed. The LF/HF ratio can be obtained by computing a ratio of the power in the LF Range divided by the power in the HF Range. This ratio may be computed for each of various segments of the data, for example, over each epoch or window of the data set. In some implementations, the ratio is calculated for equal periods of 0.5 seconds to 5 seconds, and may be computed for overlapping windows or segments of the data.

Referring again to FIG. 1, in step 135, approximate entropy can be computed. An approximate entropy algorithm can be used to estimate this heart rate characteristic. In some implementations this method can operate over 300 values of 1 Hz heart rate values derived from the higher rate EKG signal (i.e., 5 minute windows). This heart rate time series within the epoch and two parameters m, the length of compared run of data, and r, a threshold related to the amount of variation in values can be used by the method to compute the approximate entropy. Within these windows each smaller sub-window of values, e.g., 5 in this example, can be used, shifting it over each other sequence of the same length, subtracting the corresponding elements and counting the number of incidences of sliding windows where the maximum difference in corresponding elements is less than a comparison threshold. An averaging of the logarithmic sums of these values for all subwindows when combined over two different window sizes can be used to compute the approximate entropy and reveal the lack of predictability in the REM and Wake stages. The mathematic steps can be executed as follows.

A time series of data $u(1), u(2), \ldots, u(N)$ is considered for entropy analysis. A sequence of vectors is created $x(1), x(2), \ldots, x(N-m+1)$ where $$x(i)=[u(i),u(i+1),\ldots,u(i-m+1)]$$

The sequence of vectors is used to create for each $i, 1 \leq i \leq N-m+1$ $$C_i^m(r)=(\text{number of } x(j) \text{ such that } d[x(i),x(j)]<r)/(N-m+1)$$

in which $d[x,x^*]$ is defined as $$d[x, x^*] = \max_a |u(a) - u^*(a)|$$

$$\phi^m(t) = \sum_{i=1}^{N-m+1} \log(C_i^m(r))/(N-m+1) \text{ and}$$

$$ApEn = \phi^m(r) - \phi^{m+1}(r)$$

Figure 5:
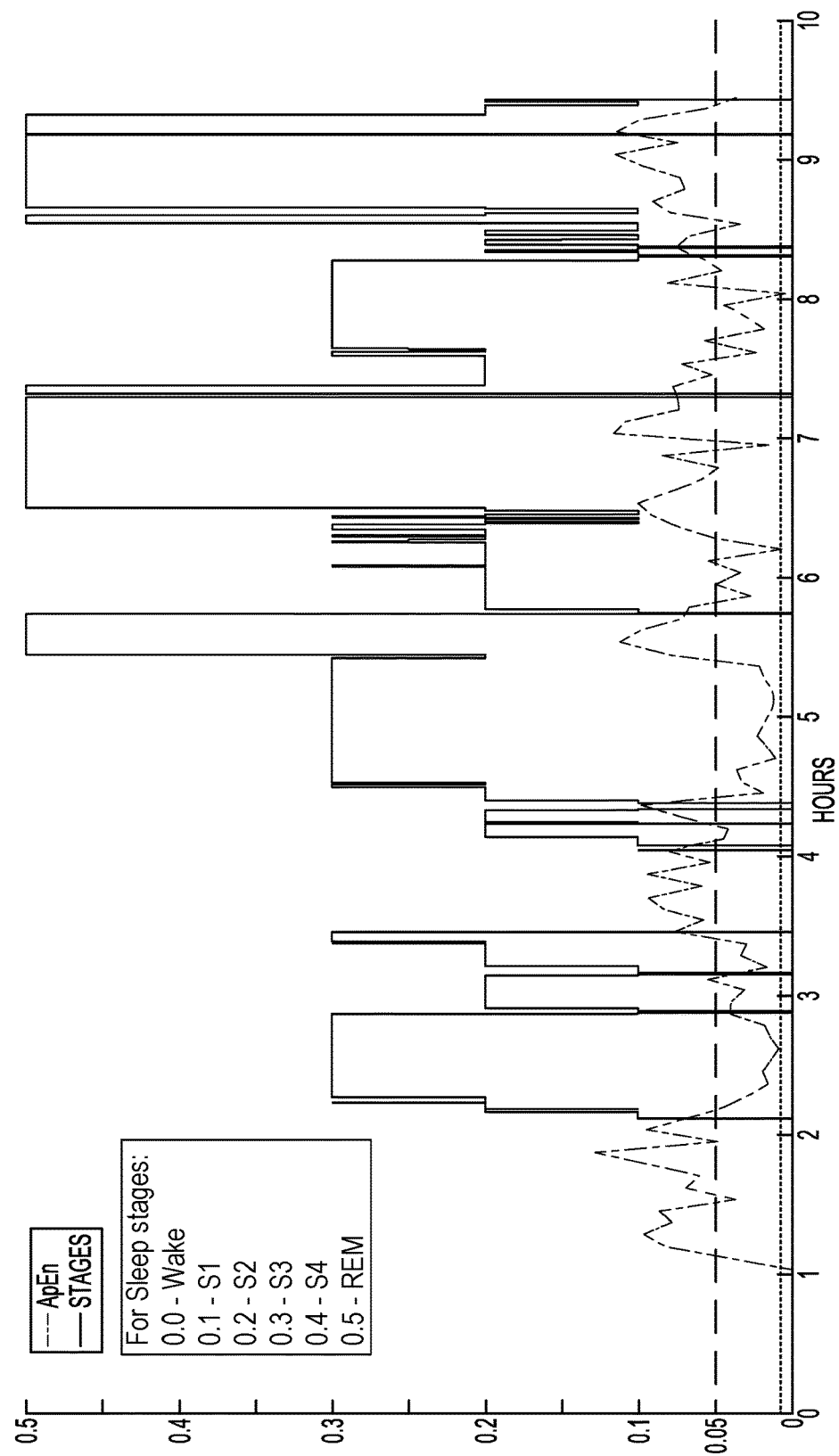
FIG. 5 is a chart illustrating sleep stages with respect to approximate entropy (ApEn) measures.

The value ApEn, representing approximate entropy, can be computed for each window in the sleep session time series for heart rate as an indicator of unpredictability for stage prediction. Alternatively, other chaos theory methods, such as discrete fluctuation analysis (DFA), can be used to create a comparable chaos indicator for the heart rate time series. A chart illustrating examples of sleep stages and ApEn values is shown in FIG. 5.

In step 140, cost function factors and weights are generated. Since multiple parameters can contribute to the prediction of each stage such as REM, SWS, etc., each of the contributing parameters can be represented as a factor varying between 0 and 1 facilitating direct comparison, weighting, and probabilistic manipulation.

In some implementations, the following factors are determined and used in combination to predict sleep stages. For each window, the mean of the window heart rate time series (meanHR) can be computed. The meanHR is compared to a fixed reference HRRestReference, which represents the expected heart rate value for resting heart rate during sleep, and to the mean of heart rates in the window time series that fall in a low percentile, HRLowReference. The resting heart rate can be used as a different value by age of the subject. In some implementations this low percentile is 50. The differences of the meanHR and these references, respectively, are converted into factors, HR Rest Comparison Factor, and a HR Low Comparison Factor using a scoring function that is defined by:

$$F(c, w, c_w) = \frac{1 - e^{rc}}{1 + e^{rc}}$$

where $$r = \log(1-w)/\log(1+w) \Big/ -c_w,$$

and where c is the scoring function's value at reference weight, $c_w$.

In some implementations, these parameters are computed using F(meanHR−HRRestReference, 0.5, 10) and F(meanHR−HRLowReference, 0.5, 10) respectively. Similar factors can be computed using the same scoring function to score the mean of all the Epoch ValueIncreaseEstimation for all epochs in the window under consideration, resulting in the WindowValueIncreaseEstimation factor.

The difference between ApEn and the mean of the lower percentile of ApEn values can be used to compute ApEn Low Comparison Factor is computed using another scoring function defined as:

$$y(x, \mu, \sigma) = e^{-0.5 \times ((x-\mu)/\sigma)^2} \sqrt{2 \times \pi \times \sigma} \text{ and}$$

$$g(x, \mu, \sigma) = \frac{y(x, \mu, \sigma)}{y(\mu, \mu, \sigma)}$$

The ApEn High Factor is computed using $F(ApEn, w_{ApEn}, c_{w_{ApEn}})$.

Various parameters may be used in the functions F( ) and g( ) discussed above. The values used for the thresholds may be determined using statistical measures of the various ApEn values. In some implementations the ApEnHighFactor is computed as F(ApEn, 0.5, ApEnMean) and ApEnLowComparisonFactor is computed as g(ApEn-ApEnMeanLow25Percentile, 0, ApEnMeanLow50Percentile) where ApEnMeanLow25Percentile and ApEnMeanLow50Percentile are the mean of the lowest 25% and 50% of all ApEn values, respectively. In some implementations, WindowValueIncreaseEstimationFactor=F (WindowValueIncreaseEstimation, 0.5, 3). In other implementations, such as for data with more peaks in the heart rate values, the value WindowValueIncreaseEstimationFactor is described as F(WindowValueIncreaseEstimation, 0.5, 5).

Figure 6:
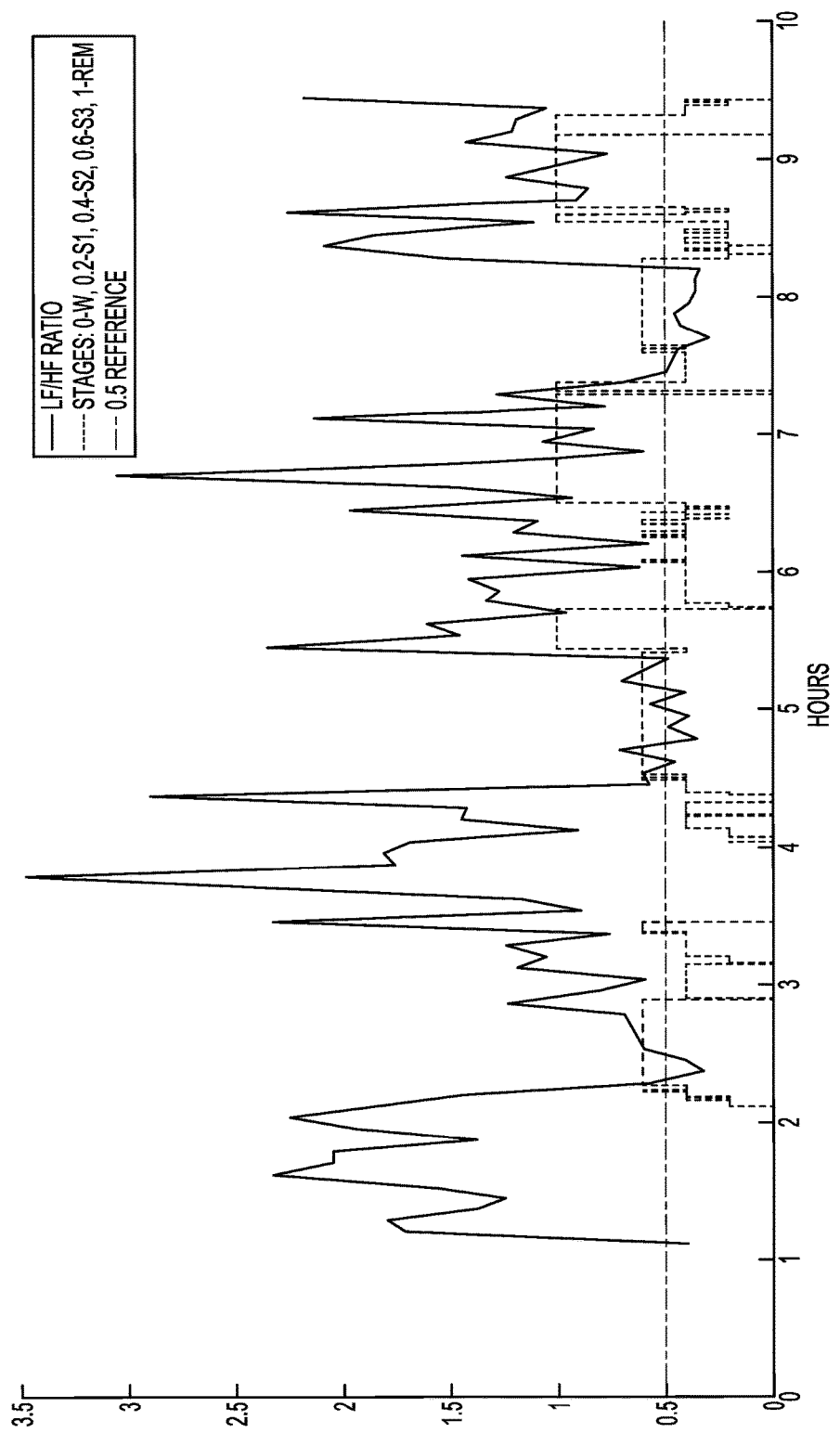
FIG. 6 is a chart illustrating an example of heart rate variability (HRV) low-frequency vs. high-frequency (LF/HF) ratios and indicators of sleep stages determined from EKG signals.

In step 145, probability scores indicating the likelihoods for different sleep stages are calculated. These scores can be determined using input from multiple types of sensors. For example, the information from motion sensors can be combined with information determined from heart rate information to produce a more accurate result. Different Probabilistic factors are created for REM or Wake probability combining the WindowValueIncreaseEstimationFactor and High Entropy factor as a mean, and for SWS combining LF/HF ratio factor and low entropy factors using a geometric mean. In another embodiment the SWS probability is directly assigned as the LF/HF ratio factor. A chart illustrating an example of LF/HF ratios and indicators of sleep stages determined using those ratios is shown in FIG. 6.

The REM or Wake probability can be considered to indicate that the stage is either Wake or REM where another discriminator can be used to distinguish between the two. Additionally, to discriminate between Wake and REM additional factors can be created to predict Wake states, which often demonstrate more dramatic spikes from resting heart rates (55-66 bpm in adults) to sudden wake heart rates of more than 80 bpm and periods of much higher entropy and variance. In devices where accelerometers and gyroscopes are available, these can be used to compute posture and activity levels over windows and use the presence of activity to enhance the probability of Wake states since REM stages, in contrast, involve highest level of inactivity and physical paralysis.

The HRV frequency analysis can also be similarly converted into factors by computing the means of the lowest 25 and 50 percentile of all the LF/HF values. $_f$The difference of the LF/HF value for each window from the lowest 50 percentile means ($d_{w,50}$) can be found in addition to the difference between the lowest 25 percentile and 50 percentile means ($d_{25,50}$). The LF/HF Low Factor is computed as $F(d_{f,50}, w_{Freq}, d_{25,50})$. A predictive probability can be estimated for the probability of the window being a SWS stage (SWSpx) by combining this factor and the minimum value of the ApEn measure for the window by using a geometric mean of ApEn Low Factor and LF/HF Low Factor with equal weights. This can be expressed with the following equation:

$$\bar{x} = \left( \prod_{i=1}^{n} x_i^{w_i} \right)^{1/\sum_{i=1}^{n} w_i}$$

Besides computing factors to determine the lowest LF/HF ratios in the data, other factors can be created to evaluate how low the ratio is when evaluated as an absolute value. In some implementations, this reference value is 0.5 and values above 0.5 are not considered to be valid for SWS stage detection. This factor, LF/HF Absolute Low Factor, is computed by weighing the difference between 0.5 and the LF/HF ratio, with higher differences generating a higher SWS probability. A predictive probability of the window being a REM or Wake stage, REMWakepx, can be computed by first using a scoring aggregation such as the weighted mean of ApEn High Factor and WindowValueIncreaseEstimation Factor. enhanced by a manipulation such as Additionally, to discriminate between the similarity in REM and WAKE characteristics an additional REMvsWakepx can be created to extract the difference in these stages with respect to sensor data. This factor uses different thresholds to exploit the general trends of higher heart-rates and entropy for Wake than in REM. Additionally, the stage duration factor is taken into account with Wake being long periods or micro-awakenings of a few seconds or a minute, and REM usually being between 5 mins to an hour. If the sensor data comprises a motion sensor, it can be used to effectively set or bolster the REM vs Wake probabilities. Detecting movement or motion, in bed or walking, imply Wake states as REM is a highly physically paralyzed state. This motion probability can be used to discriminate between Wake and REM. Another factor, REMWake Value High Factor can be created to determine how high the window values are using a geometric mean of HR Rest Comparison Factor, and a HR Low Comparison Factor. Further, if this factor is higher than a threshold the REMWakepx can be enhanced by a manipulation such as $$REMWakepx = REMWakepx^{REMwake\ Value\ High\ Factor}$$

Figure 7:
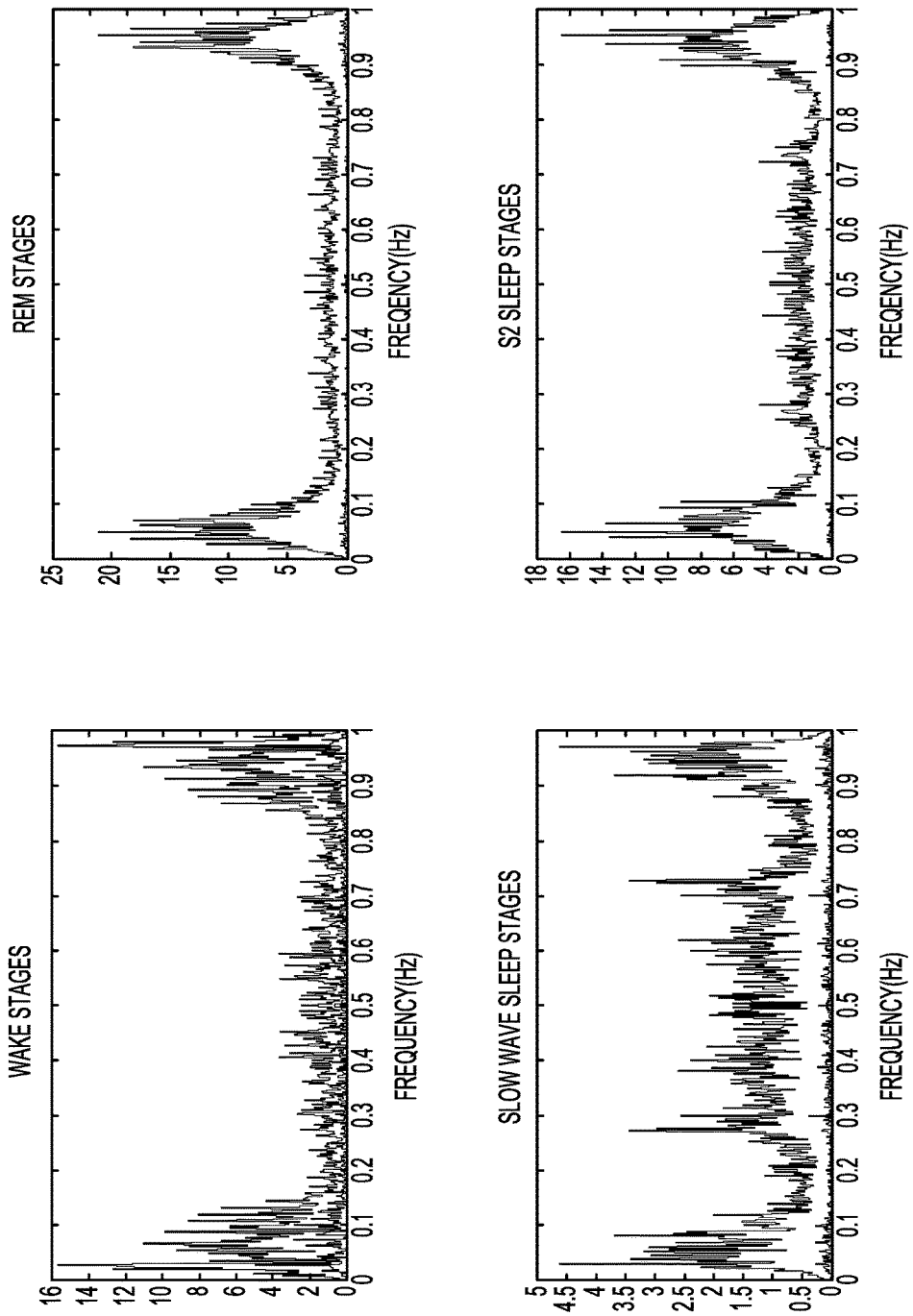
FIG. 7 illustrates examples of charts showing HRV frequency spectra for a healthy subject for wake stages (top left), REM Stages (top right), slow wave sleep (SWS) stages (bottom left), and S2 sleep stages (bottom right).
Figure 8:
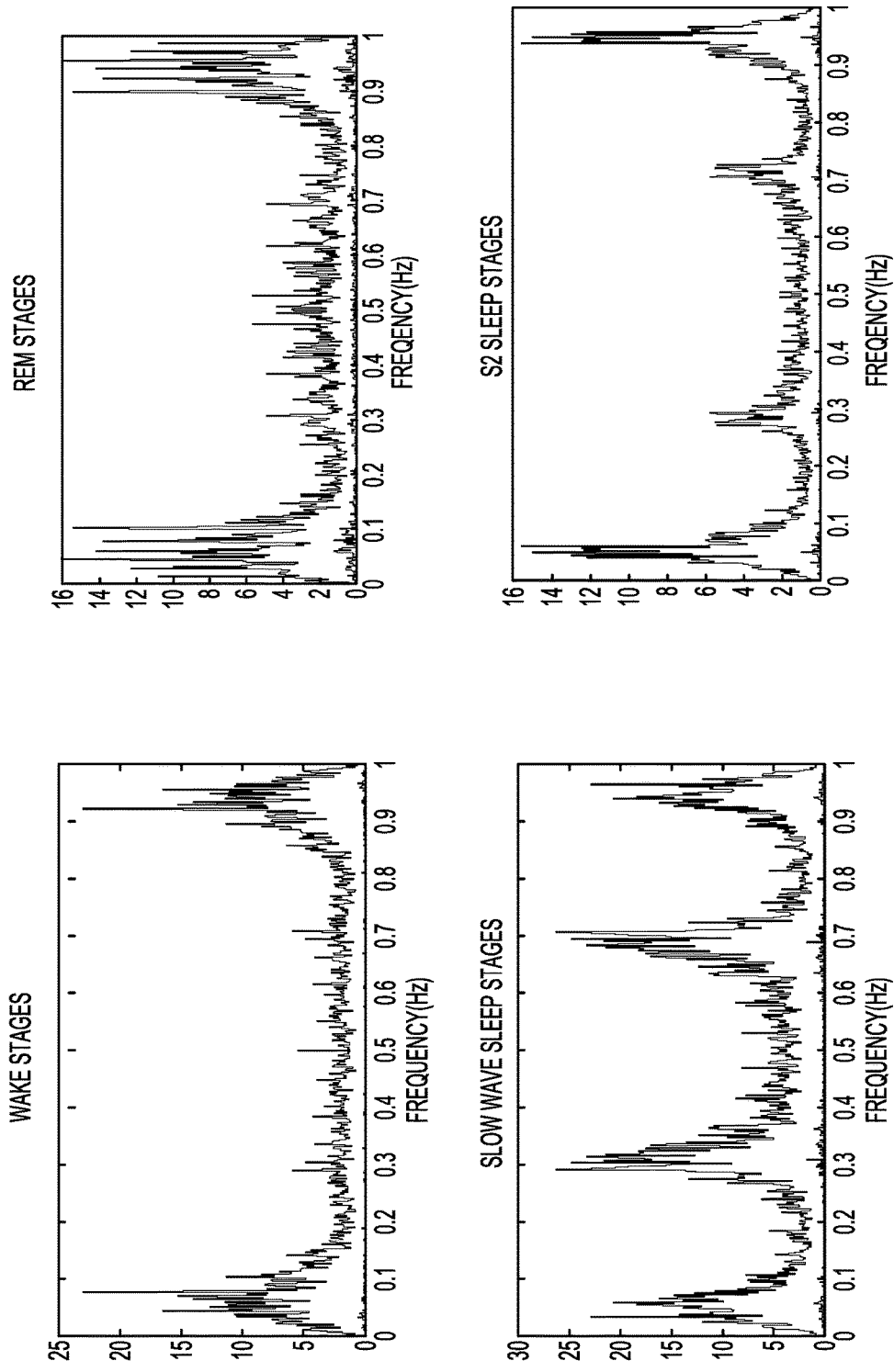
FIG. 8 illustrates examples of charts showing HRV frequency spectra for a child with ADHD for wake stages (top left), REM Stages (top right), slow wave sleep (SWS) stages (bottom left), and S2 sleep stages (bottom right).

Examples of HRV frequency spectra are shown in FIGS. 7 and 8. Each of these figures illustrates examples of charts showing HRV frequency spectra for a for wake stages (top left), REM Stages (top right), slow wave sleep (SWS) stages (bottom left), and S2 sleep stages (bottom right). FIG. 7 shows data for a healthy subject, while FIG. 8 shows data for a child with ADHD.

In step 150, stage decisions and stage assignments are made using a rule-based framework. A top layer decision-making algorithm weighs and resolves the computed predictive probabilities of stages in each window, comparing the current window's prediction with the previous/ongoing stage, the probability of transition, and rules that govern the possible transitions and the amount of stable prediction time required to actually confirm a change in stage. Each window can be assigned a stage of Light (S1 or S2), Deep (Slow Wave Sleep—S3 or S4), REM or Wake. This can be done by processing each window's stage predictive probabilities such as slow wave sleep probability (SWSpx), REM or Wake probability (REMWakepx), and REMvsWakepx, and can additionally be customized based on their experimental values and trends evaluated against technician scored stages.

Rules can be enforced necessitating the detection of light sleep stage before REM or SWS stages, ignoring Wake fluctuations within REM when less than a certain time threshold. For each window the previous stage is considered and assigned a probability to continue and the stage probabilities of the current window are compared to each other. The highest probability stage if higher than a threshold, e.g., 0.5 in some implementations, is considered as a possible stage for the window. If the highest probability stage is the same as the previous stage the method makes the assignment to the stage and continues to the next window. If the stage is different from the previous stage it is considered as a possible stage transition and checks are made to determine if the transition if feasible. If it is a REMWake stage prediction, the probability of REMVsWakepx is checked. If this is above a threshold, such as 0.5 in some implementations, the stage is considered a Wake stage else a REM stage. Based on the application, the method is being used for additional checks in patterns can be performed to minimize stage fluctuations and add additional rules that are relevant for the application cases. The windows used for these computations can range from discrete windows to sample by sample overlapping windows based on the processor speed and memory available on the system they are implemented on.

In some implementations, the stage prediction is made by a stage classifier trained on truth data, e.g., examples of inputs having actual corresponding sleep stages labelled. Examples of such classifiers include, for example, neural networks, maximum entropy classifiers, support vector machines, and decision trees. Methods and systems are described for classifying segments of a set of signals to a set of discrete decisions about said signals in the form of sleep stages. The method includes a procedure for training the system to predict sleep stages based on a set of input signals. The input signals may include sensor data or other parameters calculated from sensor data, e.g., values indicating a subject's movement, heart rate, HRV, etc. Examples of these sets of signals that have been labeled with a truth signal, e.g., data that indicates correct stages corresponding to the examples, can be used to train the classifier. The trained classifier can then be used to evaluate a set of input signals using the trained system to predict sleep stage. In some implementations, raw heart rate, smoothed heart rate, LF/HF, and approximate entropy as input signals to the classifier. Signals can be passed along with ground truth to the training system to generate a sleep stage evaluation engine, which can evaluate new input signals to produce a prediction of sleep stage.

First, a method for signal classifier training is described. The purpose of the training step is to supply a set of ground truth data for some number of subjects, along with arbitrary data that corresponds with the ground truth data in time. The system described will build a set of histograms over this data which will be used during evaluation to compute a probability distribution describing sleep stage at some point in time.

Let $N_s$ be the number of subjects to be used for training, for which ground truth data is available.

Let $$S_i(t) = \begin{cases} 0 & \text{if wake} \\ 1 & \text{if rem} \\ 2 & \text{if light} \\ 3 & \text{if deep} \end{cases}$$

be a function representing the ground truth sleep stage for multiple subjects with i representing the ith subject. More stages can be added as needed.

Let $N_f$ be the number of input functions to be used for training and classification.

Let $F_{ij}(t)$ be a set of $N_f$ functions for each individual i which correlates with each $S_i(t)$ in time. These functions are arbitrary, but could represent directly, or a variation on, sensor data taken during the sleep study.

Now define $N_f$ values $Fmin_j$ and $Fmax_j$, where $$Fmin_j = \min F_{ij}(t) \text{ for all } i,t$$

$$Fmax_j = \max F_{ij}(t) \text{ for all } i,t$$

These are the minimums and maximums of each function j computed over all subjects.

Finally we define $N_f \times 4$ histograms $H_{js}$ with N bins where each bin value is equal to the sum of number of samples of j for all individuals i in which $F_{ij}(t)$ falls into the bin for a given sleep stage s.

Stage s is known by looking up the ground truth in $S_i(t)$. The bin's index is computed as $$b_j = \text{floor}((F_{ij}(t) - Fmin_j)/(Fmax_j - Fmin_j) \times N)$$

These histograms represent a trained system which can be used for classification. From an intuitive point of view, they represent for any given sleep stage s and function j, how the function's value at any time t correlate to a given sleep stage.

The number of input functions is also arbitrary, but should be fixed between the training and classification steps. New training data can be added to an already trained system, so long as the values of the new training data fall within Fminj and Fmaxj of the already trained system. If they do not, the system can be retrained using the old and new training data.

Now a method for classification of a set of functions into a sleep stage probability distribution is described. For classification, the input is the same set of input functions $F_{ij}(t)$, except without ground truth $S_i(t)$.

We define stage count as $$C_s(t) = \sum_{j=0}^{N_f} H_{js}(\text{floor}((F_{ij}(t) - Fmin_j)/(Fmax_j - Fmin_j) \times N))$$

Finally, we compute a distribution describing the probability of any sleep stage at some time as $$P_s(t) = C_s(t)/\Sigma C_s(t)$$

$P_s(t)$ can then be used to estimate sleep stage in an individual at some point in time.

In some implementations, the following $F_{ij}(t)$ are used as input:

Let $F_{i0}(t)$ be raw heart rate as received from a heart rate monitoring device.

Let $F_{i1}(t)$ be approximate entropy of $F_{i0}(t)$.

Let $F_{i2}(t)$ be LF/HF of $F_{i0}(t)$ where LF is the low frequency component of the Fourier transformation of $F_{i0}(t)$ and HF the high frequency component.

Let $F_{i3}(t) = \text{ExpAvg}(F_{i0}(t)) - \text{Median}(F_{i0}(t))$ where ExpAvg (F) is computed as an exponential average of F starting from the first sample, and using a weighting of 0.99.

In some implementations, other sensor data can be used as input. This includes but is not limited to: audio, inertial measurements, EEG, temperature, and any mathematical transformations of these measurements. Breath detection can be performed using an audio signal, which can be transformed into breathing rate and used as an input to the system described. Inertial measurements could be used directly, as there is likely to be more movement during the wake phases, which makes the signal directly useful. In some implementations, EEG is used by sleep technicians to produce the ground truth input to this system, thus they are also directly applicable. In some implementations, the intermediate probabilities and factors described above such as Apen Low Factor, SWSpx, REMWakepx, LF/HF Low Factor, WindowValueIncreaseEstimation Factor are also used to train and classify stages. In some implementations functions representing EEG based stage probabilities, for increased delta waves or alpha waves observed, and EOG based stage probabilities for REM stages are created and used as an input to the stage classifier. This can allow the same fusion method described herein to predict sleep stages using new sensors as the technology to make them suitable to a particular application emerges.

In addition, functions not directly tied to sensor data can also be used. A sleep stage probability function over time can be used as input, where the value of this function changes based on known constraints of normal human sleep. For example, deep sleep is more likely to occur earlier in sleep, and thus a deep sleep probability function would have a high value when sleep is first detected, and trail off toward zero over time or as deep sleep phases are detected. This relative time sleep stage function can indicate that REM, especially longer REM periods are much more likely in the second half of the sleep session, with some smaller REM periods in the first half.

Additionally, for people in general, or an individual and absolute time function can be created since a person's circadian rhythm causes similar stages to occur night to night. Therefore, for a particular person the probability of having deep sleep between 4 am and 5 am may be very low. A function representing durations of a sleep stage in the time neighborhood can be used to assign the probabilities of longer deep sleep sessions, with possible other stage interruptions in the first half of the night and similar sessions of REM in the second half. Additionally, it can be used to limit the fact that REM sessions of greater than 1 hr are highly unlikely and may suggest a stage such as Wake.

Once the probability function $P_s(t)$ has been computed using the described method, a final decision for sleep stage at some time can be made. In some implementations, a stage is chosen for each point in time as the max over s of $P_s(t)$. In another embodiment, constraints can be applied when making a decision. Constraints can include those which do not allow specific transitions to occur since they are unlikely based on knowledge of human sleep behavior. For example, a transition from awake to deep sleep is unlikely, so even when such a deep phase is computed to have the highest probability using this method, the next highest probability stage is chosen due to this constraint.

In another embodiment, a neural network can be used to compute a final decision for sleep stage. The input to this network would be the probability functions $PP_s(t)$ for some time t, as well as some number of decisions for previous times. This network would be trained using the same ground truth data used to train the classification system described. The output from the network would be a sleep stage decision for a single point in time.

The methods of combining multiple inputs can be used to classify finer stages such as S1, S2, SWS, REM, and Wake as data is available. They can also be used to train and classify simpler high precision Wake vs Sleep classification. Additionally, this can be performed by post combining all the sleep specific stages of light, deep and REM into a SLEEP category.

Figure 9:
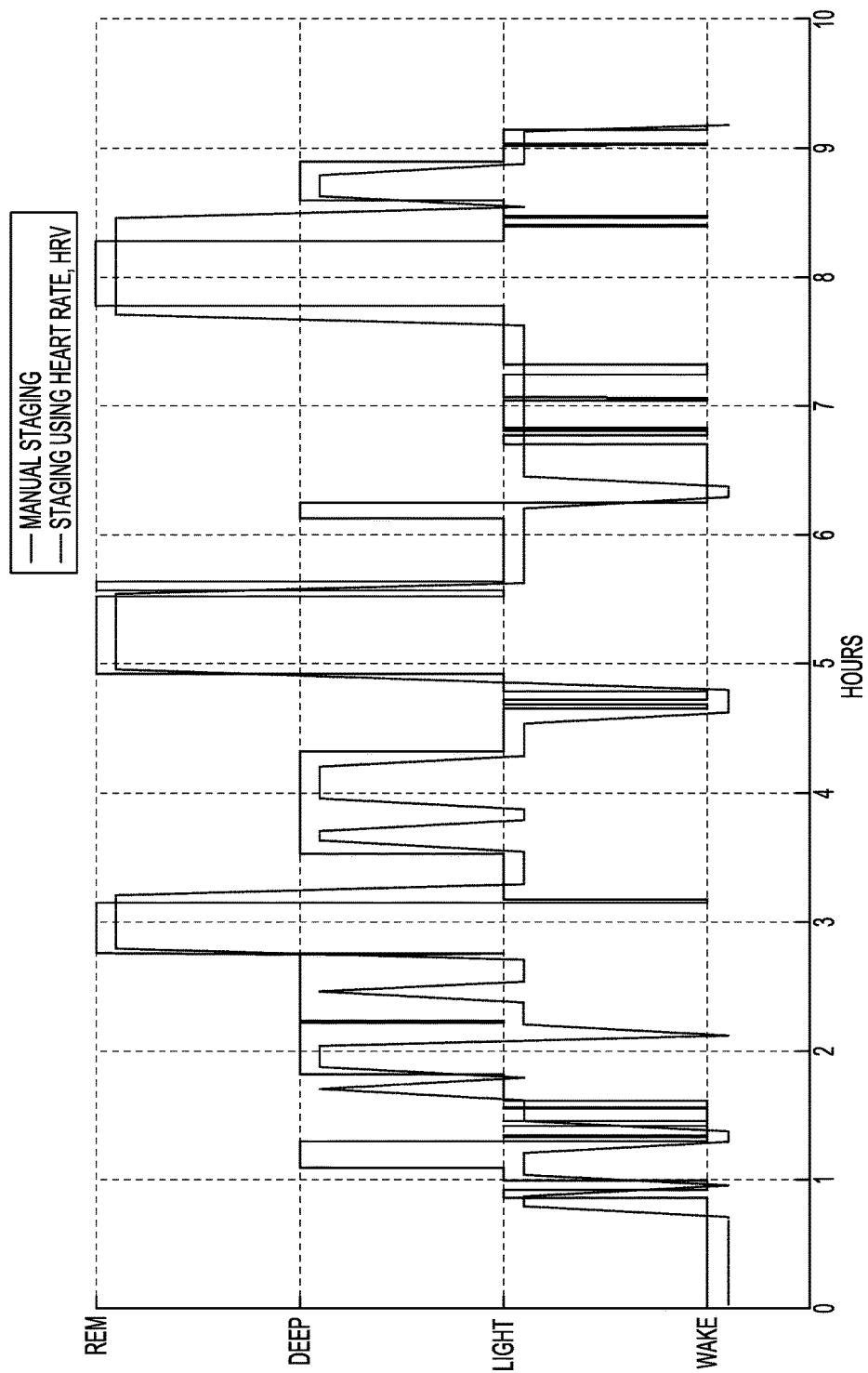
FIG. 9 is a chart illustrating an example of staging (Light-S1 & S2, Deep-SWS, REM, Wake) for a healthy subject using the techniques disclosed herein, versus results of manual staging. The chart demonstrates effective staging of the disclosed techniques, including for REM and SWS stages.

FIG. 9 shows the method's performance compared to sleep studies in a sleep clinic. To produce the results illustrated, the system takes as input the two-lead EKG signal in the PSG Sleep Studies. In some implementations, the techniques disclosed herein and results of sleep lab manual analysis were found to agree a majority of the time, for example, 95% of the time for Wake, 82% of the time for REM, and 62% of the time for SWS.

The performance of the embodiments reduced to practice are comparable to the inter-rater reliability of different human scorers as reported by the AASM Visual Scoring Task Force which reported 78-94% agreement for REM (3 studies), 68-89% for Wake (3 studies) and 69% for SWS (2 studies). Another study by the task force examining 3 technicians rescoring 20 studies after a median of 6.5 months resulted in (self) agreements of 89-93% for Wake, 72-88% for REM and 55-75% for SWS. Thus, our algorithm is as effective as the human technicians studied in these reports.

The source of the data, for the method and system disclosed herein, can be from PSGs in a sleep laboratory or sensors worn on the body. In some implementations of this invention, the source of the sensor data is a wearable device. The methods can be used on any device providing EKG signals or derived heart rate. The data could also be pulse rate from devices such as pulse oximeters, pulse-meters or pulse monitors in the form of watches such as the Apple Watch, Samsung Gear watches, and other fitness monitors. Some of these devices may use photoplethysmography (PPGs) to estimate pulse rate. Methods for determining posture and sleep duration and quality using motion sensing can take input from any quality accelerometer and gyroscope combination. Any off-the-shelf motion sensor with even a single axis accelerometer can be used to enable the methods disclosed herein, along with light sensors and microphones with varying sensitivities when available. Any EKG source or derived heart rate sensor or pulse-rate monitor such as wearable watches can be used by the methods disclosed herein to analyze sleep events and detect sleep staging.

The microphone audio signals, when available, can be used to detect sleep apnea events and breathing patterns and rates. This can be implemented using pattern matching methods or neural networks trained on data from patients with obstructive sleep apnea. In this process, stretches or windows of audio data are normalized to a fixed time length and tested on neural networks trained for apnea detection. The above sleep stage classification functions can be improved using factors that represent that apnea events are much less likely during deep sleep. This data is available in several databases of clinical trials. Additionally, heart rate variability (HRV) can be further used to bolster the methods tracking the characteristics in heart rate patterns and HRV frequency spectrums when the subject stops breathing, restarts breathing and other apnea related events.

Figure 10:
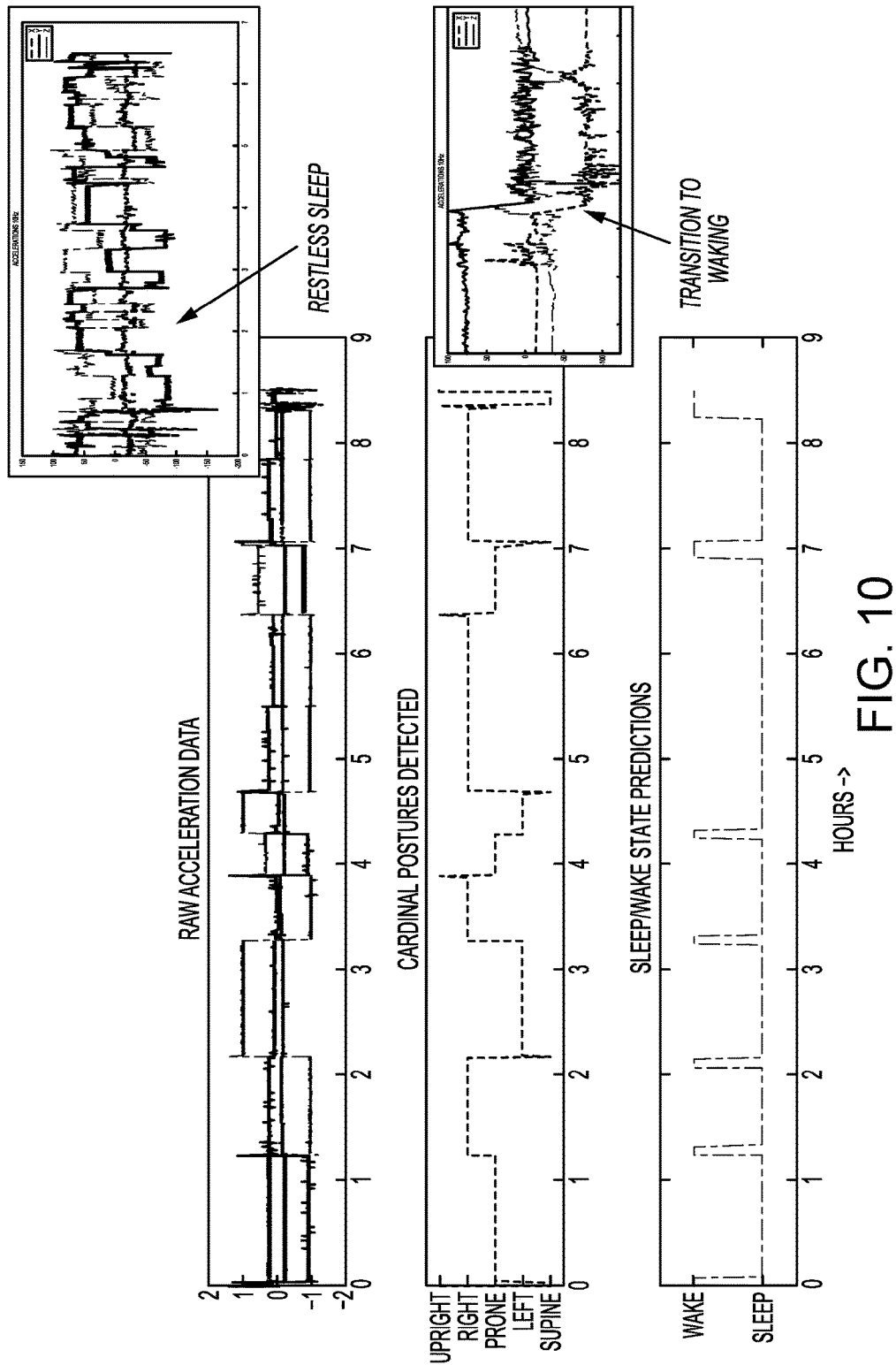
FIG. 10 is a chart illustrating correlation of motion data with Sleep/Wake detection during sleep.

Referring to FIG. 10, accelerometer or gyroscope data can be used to improve discrimination between Wake and REM stages. In addition, they can be used to approximate sleep and wake states, based on motion detection. Step detection where the posture of the person has changed to an upright position and detection of walking signatures can confirm the subject to be awake except in the extreme case of sleep walking. These can be used to enhance REMvsWakepx. Movement during lying down or sitting can be used to determine whether a person is asleep or lying down or sitting still. Movement variances and magnitudes can also be used to determine how restful a subject's sleeping patterns are. This can be achieved by aggregating motion sensor data, accelerometer and gyroscope data in epochs over the sleep session. In some implementations, this epoch size is 30 seconds. The variances, maximums, minimums, averages are computed for each epoch and then aggregated for bigger windows. In some implementations, this larger window can be 5 minutes. This hierarchical comparison and aggregation can be used for larger windows such as combining 5-minute windows into 30-minute larger windows. This can enable movement and their effects to be analyzed by logic and reason in these larger windows. This allows a small movement while changing posture preceded and followed by no movement to be categorized as a posture change rather than a long wake state. Multiple occurrences of movement are therefore weighted higher than single spikes of movement, which may occur while changing position or other movement in the sleep environment unrelated to the subject.

As shown in FIG. 10, motion data can include raw acceleration data. From this data, and potentially other sensors, various cardinal postures can be detected. From the accelerometer data and/or the detected postures, a sleep/wake prediction can be generated. This information may be used to validate staging results using heart rate, as a factor in the calculations for stage likelihoods, as input to a sleep stage classifier, or in another manner.

Figure 11A:
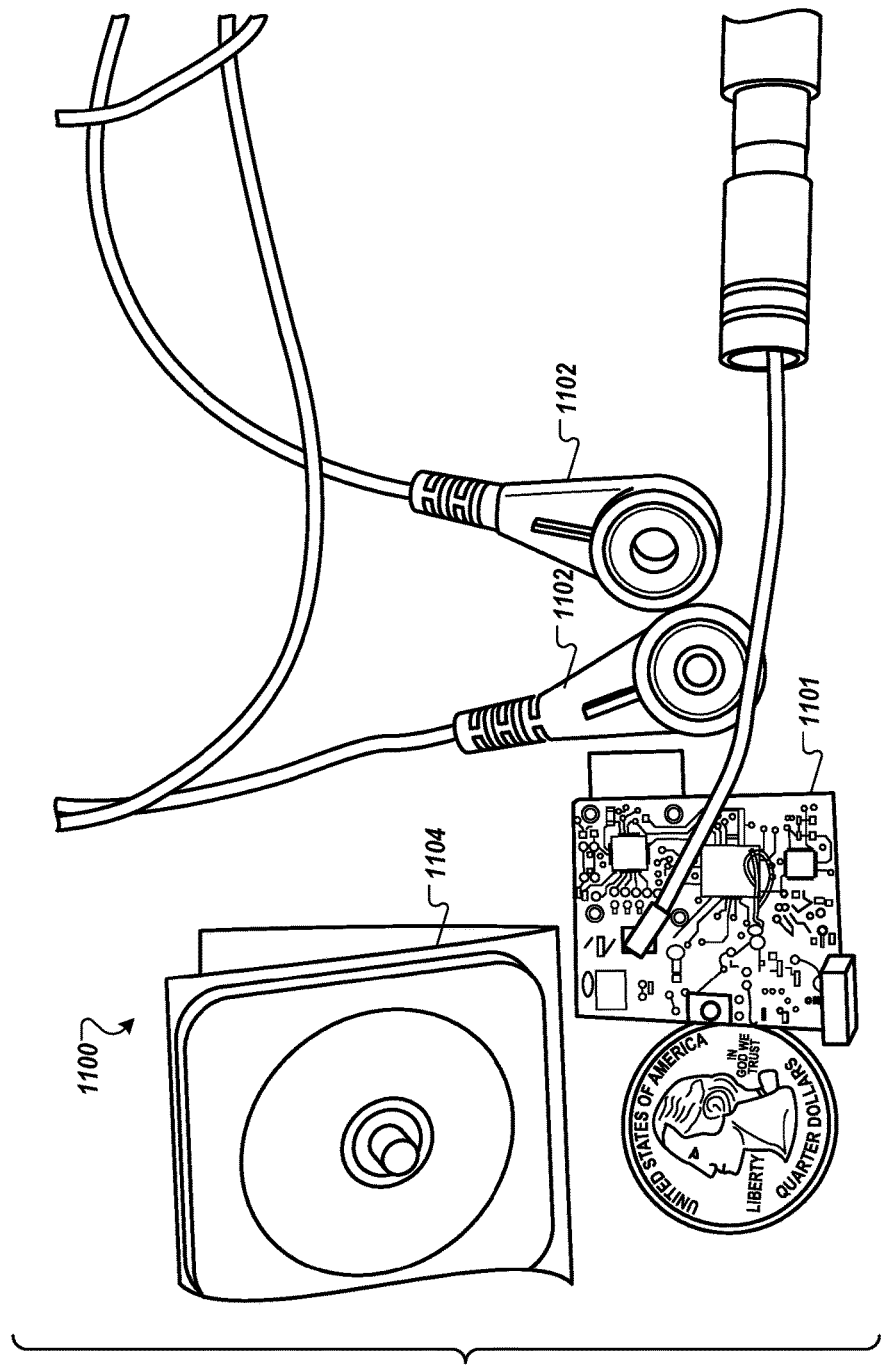
FIGS. 11A and 11B are illustrations of an example of a wearable body data recorder.
Figure 11B:
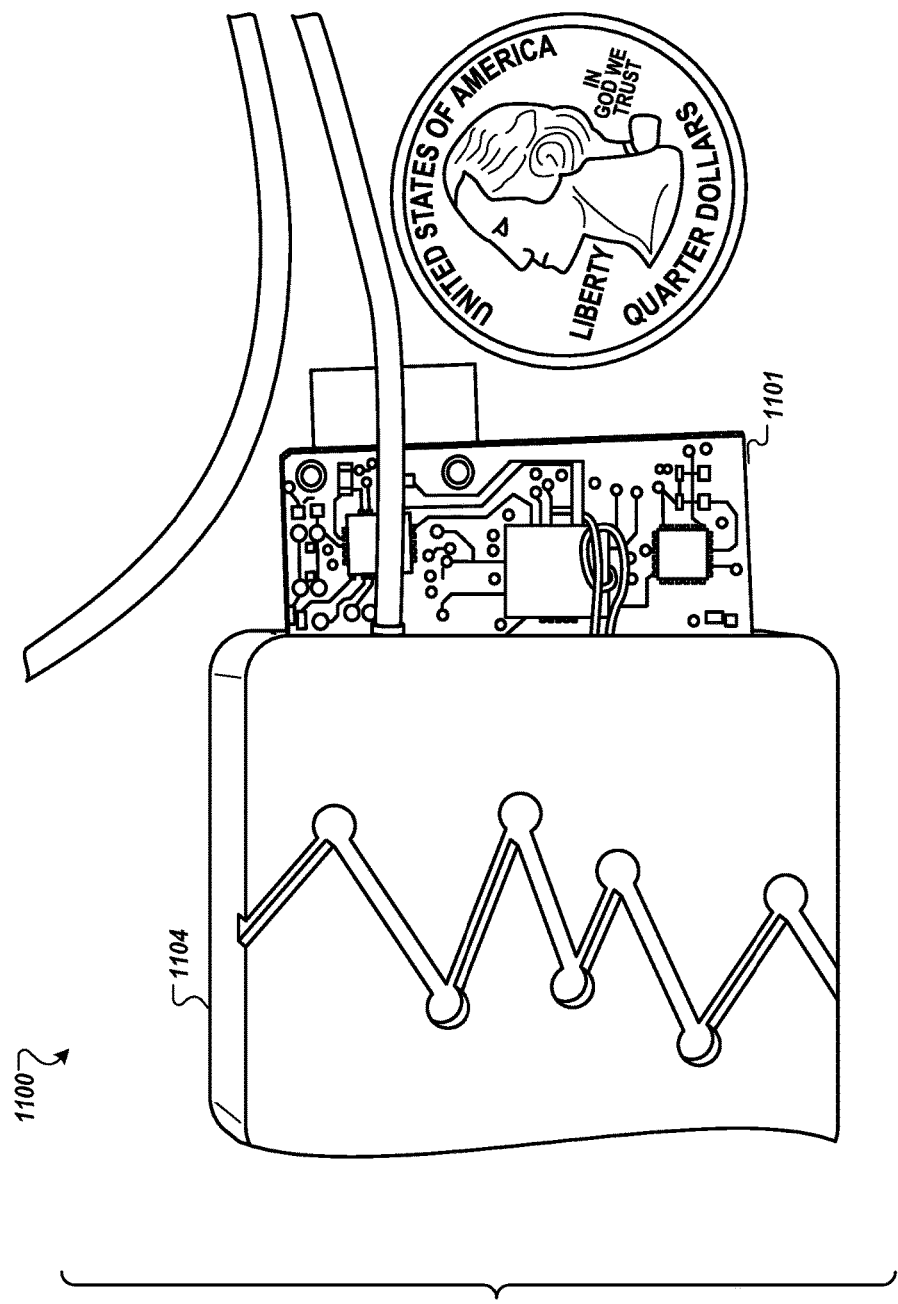

Referring to FIGS. 11A and 11B, in some implementations, the source of the data is a miniature wearable device 1100, referred to herein as a Body Data Recorder (BDR). The BDR which has been reduced to practice as a dual-sided 4-layer circuit board designed to achieve a miniature form factor (~1 inch$^2$) housing 3-axis accelerometers, 3-axis gyroscopes, microphones, heart rate sensors, temperature, and light sensors, among others. An image of a U.S. quarter dollar coin is included in FIGS. 11A and 11B as a visual size reference showing the scale of the device 1100.

For the example illustrated, the combination of sensors has been selected since the data provided can be used for detection of sleep staging with acceptable scoring accuracy, and for recording ambient signals of light and sound to assess the suitability of the environment and in tracking adherence to clinician recommendations. The device also supports detecting and quantifying apnea events and snoring using a built-in microphone. Specifically, the above features can be achieved and provided in a small form factor at an affordable price. The small form factor allows the device to be worn in a location such as the chest all night or day for multiple nights without causing discomfort. This can be critical to the target application.

The body data recorder has been designed to be small, low power, and to fit comfortably in clothing, where the contacts can even be provided using conductive polymer. The BDR can operate independent of other devices, without any cords or cables connected to a computer or other device not worn by the patient. The parts selected and populated on the dual-sided board for this embodiment include the following specific components, though alternatives will be apparent to those skilled in the art: an AD8232 providing single lead heart rate monitoring and serves as an integrated conditioning block for ECG and instrumentation amplification sampling up to 2 kHz, Invensense 6 degree of freedom Inertial Measurement Unit (MPU6500), Knowles MEMS omnidirectional microphone with 100 Hz~10 kHz and −18 dB±3 dB sensitivity, TEMT-6000 high photo sensitivity ambient light sensor from Vishay Electronics, TMP102 temperature sensor from Texas Instruments, U.FL connector for delocalization of sensor pads via a miniature RF connector for high-frequency signals up to 6 GHz manufactured by Hirose Electric Group, Communications: microSD, low power bluetooth (BLE) from Microchip, 1000 mah Li polymer battery, sensor cables, and sensor pads (3M) and 3-D Printed prototype packaging. A circuit board 1101 on which data storage, sensors, processing devices, etc. are mounted can be places in a protective housing 1104.

Any appropriate off-the-shelf motion sensor with even a single axis accelerometer can be used to enable the methods disclosed herein, along with light and microphones with varying sensitivities, when available. Any EKG source or derived heart rate sensor or pulse-rate monitor such as wearable watches can be used by the methods disclosed herein to analyze sleep events and detect sleep staging.

The two EKG sensor pads 1102 can be worn below the pectoral muscles (i.e., on the rib cage—left and right). This location has been selected after experimentation to reduce muscle activation artifacts in the EKG signal. The system produces similar results for being worn with the right electrode on the pectorals and the left under the pectorals and several other electrode placements. In some implementations, these sensor pads are provided via conductive polymer that can be built into a t-shirt or garment.

In another embodiment, the device can support both 3-lead and 2-lead EKG sensor pads, where the thigh is where the $3^{rd}$ EKG lead is connected for higher EKG amplitude. In this embodiment, the device is equipped with Wi-Fi to communicate with routers, mobile phones to transfer data. Wi-Fi can be used in this embodiment to upload sensor or processed data to servers for storage or to execute further processing to achieve goals such as stage classification or apnea event detection. In this embodiment the light sensor is a TAOS TFL2561FN, and the microphone an Invensense INMP401. A digital signal processor from Microchip is used to ensure high sampling rate logging to the microSD card of all sensors, long device life and upload and transfer via Wi-Fi. An ESP8266 Wi-Fi module is used for the Wi-Fi communications.

The methods described herein can be implemented completely or partially on these or other similar devices, or on mobile devices, such as smartphones. The processing can be shared among these devices and even a remote server to aid processing power and device battery life.

A comprehensive sleep monitoring and analytics system can include a device that records sleep data, a mechanism for the subject to enter data, a communications link for data and entries to be transferred to a computer system, the methods disclosed herein to convert the data into sleep results, such as sleep stages and events, and methods to generate clinical reports from the data and results.

Figure 12:
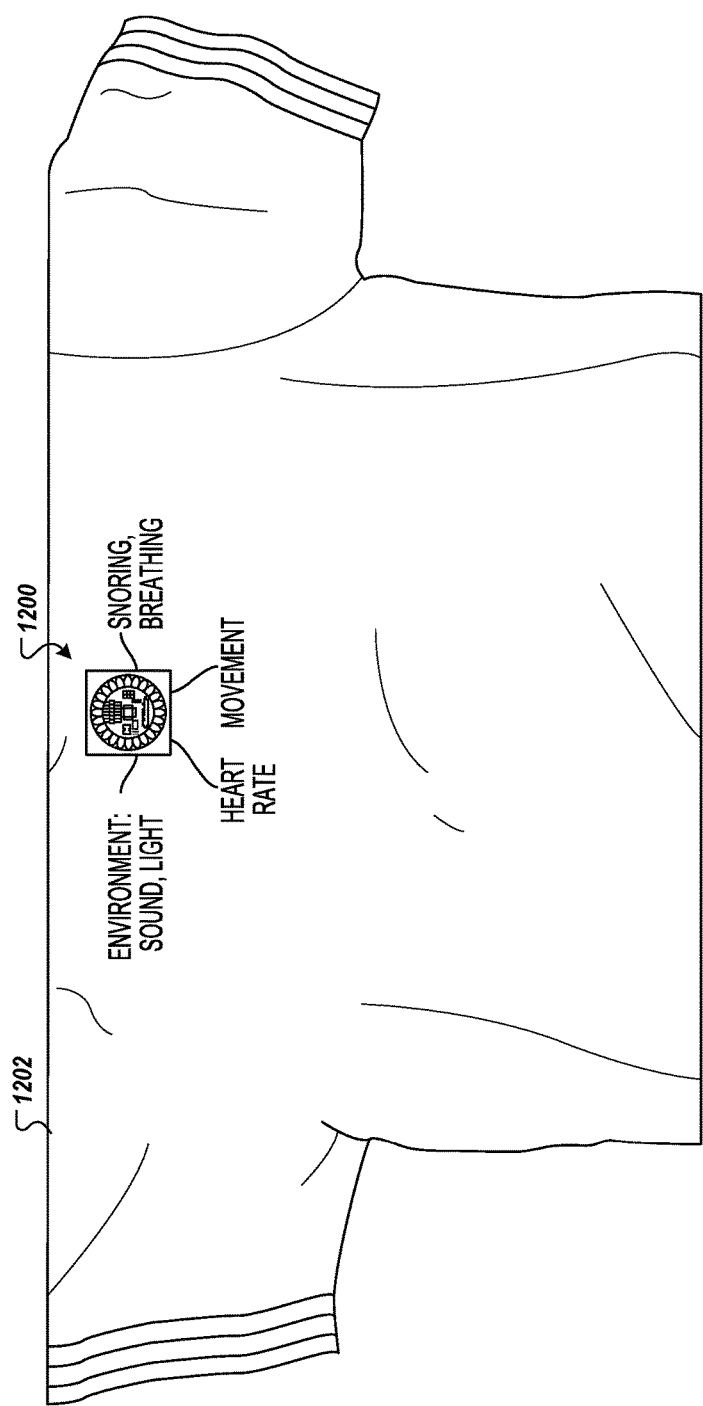
FIG. 12 is an illustration of an example of a T-shirt housing wearable sensors, for use with a body data recorder.

Referring to FIG. 12, in some implementations, a body data recorder 1200 may include a t-shirt 1202 or other garment that houses multiple sensors. The t-shirt can be worn by the subject during sleep sessions, or even all day if the subject chooses.

Figure 13:
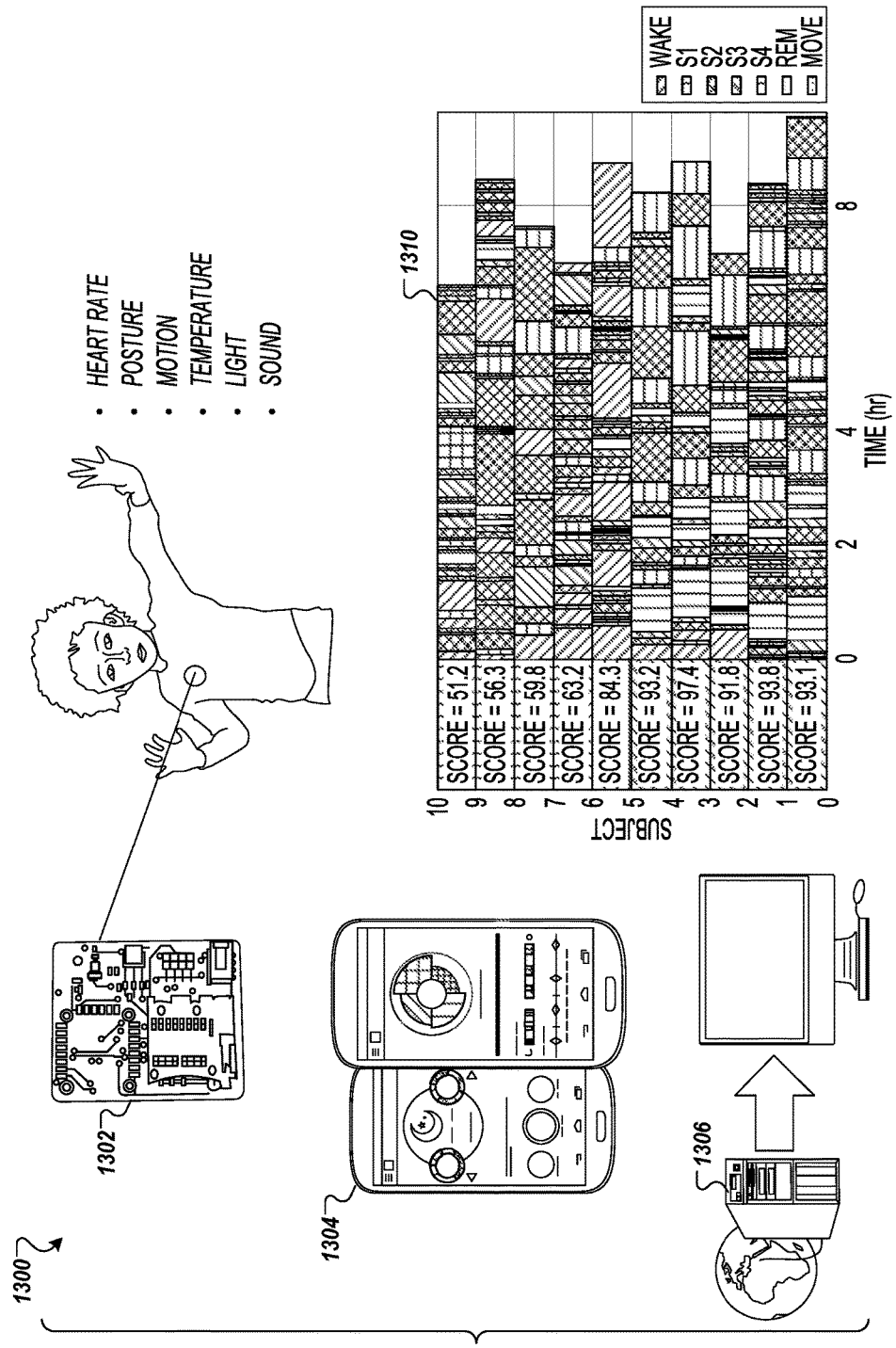
FIG. 13 is a conceptual drawing illustrating example of the components of a sleep monitoring system.

Referring to FIG. 13, a system 1300 for measuring sleep information and performing sleep staging can include a BDR 1302 with multiple sensors, a mobile device 1304 that communicates with the BDR 1302, and a server 1306. The data from multiple sensors of the BDR 1302 is recorded and can be transferred to a mobile application of the mobile device 1304 via a wireless link such as Bluetooth or low energy Bluetooth. The mobile application also enables the subject to make the diary entries of sleep times, moods, habits, and sleep satisfaction questionnaires. The mobile application also enables the subject to take reaction time tests.

The mobile application can upload the data to the server 1306 over a link such as Wi-Fi or cell links. Alternately, the data can be transferred from the device or the mobile app via Bluetooth or Wi-Fi to a computer system or via a cable connection. The server 1306 can host the methods to translate received data into sleep results i.e., sleep stages (hypnograms) and sleep events (e.g., apnea detection, sleep walking, snoring).

Examples of hypnograms are shown in chart 1310. In some implementations, raw sensor data is provided to the server 1306. In other implementations, to conserve power and manage bandwidth constraints, the BDR 1302 may perform at least some of the processing of the heart beat data, which reduces the amount of data that must be transferred. Thus the BDR 1302 and the server 1306 may together perform the functions described with respect to FIGS. 1 and 2.

The methods to generate sleep results and reports can be housed on the computer system. They can additionally or alternatively be hosted on or communicated to the mobile application of the mobile device 1304 or even on the BDR 1302. In consumer applications, the results i.e., hypnograms, long term views, sleep events etc. can be displayed daily and over long periods of time for the subject to view along with their Sleep Score, Subjective Sleep Score and any other sub-scores. These can be also be plot against performance and habits to enable the subject to identify trends in their sleep and correlations between different sleep variables (e.g., total sleep time vs coffee intake). In a clinical use of this embodiment, the system may be prescribed to the subject by a clinician to be used for a certain period of time, usually multiple nights (e.g., 7-10 days). The subject can take the system to their home environment, or elsewhere, and wear the device while sleeping and interact with the app. The data is processed by the mobile application and uploaded to the server over the communications link, where the data is converted into a clinical report that is delivered to the clinician's office. The report can include adherence tracking to assist in behavior changes and therapy and efficacy tracking.

The wearable device can also be worn beyond sleep sessions or even all day, where coupled with analytical processes, activity and performance can also be monitored.

In some implementations, occurrences of stress and anxiety are also detected and scored. Stress and anxiety can be distinguished from high intensity physical exercise using a combination of HRV analysis and neural networks. For specific cases such as developmental disorders, patterns such as rocking, seizures etc. can be detected and even mapped by time and location when location systems are available to the analytics.

In the clinical setting, the clinician can view the hypnograms revealing the sleep stages as a part of a report generated. These can include hypnograms for multiple days. The clinician based on these can infer if the subject's sleep architecture has abnormalities, e.g., lacks SWS sleep, low REM sleep, large number of awakenings, apnea events etc. The clinician may use the results of staging and events to offer the subject actionable suggestions (e.g., Cognitive Behavioral Therapy—CBT). These may include actions such as decreasing the amount of time spent in bed to reduce laying in bed awake, lowering the temperature of the room, increasing exercise in the morning, etc.

The methods herein can be implemented on devices such as smartwatches, smartphones or health monitors that provide pulse rate or heart rate and possibly motion data. In these cases, the methods can be used to determine stages and events, score sleep quality and display it to the user as part of a health monitoring application. The user can adjust their lifestyle patterns based on this sleep information displayed over multiple days or longer periods of time. Additionally, this information can be supplied to clinicians through patient-clinician correspondence or integration into Electronic Health Records (EHRs). This can be even more relevant for consumer devices with FDA clearance or similar certification aimed more at clinical data.

The results of staging in consumer and other applications can be used by a system for various applications. Some of these may include sending a message to a third-party system about what sleep stage the subject is in, waking up consumers who wish to lucid dream during certain REM or dreaming stages, and displaying sleep stages to the subject the next morning or in real-time. Displays can be made to the subject for the results of the methods disclosed herein using any computer system with a screen such as a laptop or mobile phone.

Embodiments of the invention and all of the functional operations described in this specification may be implemented in digital electronic circuitry, or in computer software, firmware, or hardware, including the structures disclosed in this specification and their structural equivalents, or in combinations of one or more of them. Embodiments of the invention may be implemented as one or more computer program products, i.e., one or more modules of computer program instructions encoded on a computer-readable medium for execution by, or to control the operation of, data processing apparatus. The computer readable medium may be a non-transitory computer readable storage medium, a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any form of programming language, including compiled or interpreted languages, and it may be deployed in any form, including as a stand-alone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non-volatile memory, media, and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, embodiments of the invention may be implemented on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any form of sensory feedback, e.g., visual feedback, auditory feedback, or tactile feedback; and input from the user may be received in any form, including acoustic, speech, or tactile input.

Embodiments of the invention may be implemented in a computing system that includes a back end component, e.g., as a data server, or that includes a middleware component, e.g., an application server, or that includes a front end component, e.g., a client computer having a graphical user interface or a Web browser through which a user may interact with an implementation of the invention, or any combination of one or more such back end, middleware, or front end components. The components of the system may be interconnected by any form or medium of digital data communication, e.g., a communication network. Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments may also be implemented in combination in a single embodiment. Conversely, various features that are described in the context of a single embodiment may also be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Thus, particular embodiments of the invention have been described. Other embodiments are within the scope of the following claims. For example, the actions recited in the claims may be performed in a different order and still achieve desirable results.

What is claimed is:

1. A method performed by one or more computing devices, the method comprising:

obtaining, by the one or more computing devices, sensor data generated by one or more sensors over a time period while a person is sleeping;

dividing, by the one or more computing devices, the time period into a series of intervals;

analyzing, by the one or more computing devices, heart rate and the changes in the heart rate of the person indicated by the sensor data over the intervals, wherein the analysis comprises:

determining approximate entropy measures indicating approximate entropy of a heart rate of the person for each of the intervals, comprising determining a series of heart rate values corresponding to different times within each interval and assessing multiple sliding windows of the heart rate values within each interval;

generating a heart-rate variability (HRV) signal for each of the intervals, performing a frequency analysis of the HRV signals, and generating HRV ratios each indicating a ratio of low frequency components of the HRV signal to high frequency components of the HRV signal; and determining a relative heart rate measure for each of the intervals, each relative heart rate measure being determined based on multiple different windows over a series of sub-interval epochs within the interval, wherein the relative heart rate measure for an interval is determined based on comparisons, for each particular epoch of at least some of the epochs, of a heart rate measure for the particular epoch with heart rate measures for epochs that occur before and after the particular epoch in the window corresponding to the particular epoch;

obtaining sleep stage likelihood scores determined by multiple different sleep stage analysis functions based on the approximate entropy measures, the HRV ratios, and the relative heart rate measures, comprising:

determining, based on one or more of the approximate entropy measures and one or more of the relative heart rate measures, a first score indicating a likelihood that the sleep stage for a particular portion of the time period is in a set consisting of a REM stage and a wake stage; and determining a second score to discriminate between the REM stage and the wake stage, the second score being determined based on (i) a measure representing a comparison of a measure of heart rate during the particular portion with a resting reference heart rate for the person and (ii) a level of movement of the person during the particular portion of the time period;

assigning, by the one or more computing devices, sleep stage labels to different portions of the time period based on a combination of the likelihood scores from the multiple different sleep stage analysis functions; and providing, by the one or more computing devices, an indication of the assigned sleep stage labels.

2. The method of claim 1, wherein obtaining the sensor data, dividing the time period into a series of intervals, and analyzing the heart rate and the changes in the heart rate are performed by a wearable, battery-operated device, wherein the wearable device includes sensors that detect the sensor data.

3. The method of claim 2, further comprising providing, by the wearable device, results of analyzing the heart rate and the changes in the heart rate to a second device for transmission to a server system; and
   wherein assigning the sleep stage labels and providing the indication of the assigned sleep stage labels are performed by the server system.

4. The method of claim 1, further comprising:
   obtaining data sets indicating signals or function outputs, the data sets being labeled with sleep stage labels corresponding to the data sets; and
   training a sleep stage classifier based on the data sets to produce output indicating likelihoods that input data corresponds to a sleep stage from among a set of sleep stages.

5. The method of claim 4, further comprising:
   determining, for each of the signals or function outputs, a signal range histogram for the signal or function output; and
   using the signal range histograms to train the sleep stage classifier.

6. The method of claim 1, wherein determining the relative heart rate measure for a particular interval comprises:
   determining, for each particular epoch of multiple of the epochs in the particular interval:
      an average heart rate for a particular epoch in the particular interval;
      a first reference value based on average heart rates for a threshold number of epochs immediately before the particular epoch; and
      a second reference value based on average heart rate for a threshold number of epochs immediately following the particular epoch;
      determining a first difference between the average heart rate for the particular epoch and the first reference value for the particular epoch;
      determining a second difference between the average heart rate for the particular epoch and the second reference value for the particular epoch; and
      determining an epoch-level relative heart rate measure for the particular epoch based on the first difference and the second difference; and
   determining, as the relative heart rate measure for the particular interval, an interval-level relative heart rate measure as an average of the epoch-level relative heart rate measures for multiple the multiple epochs in the particular interval.

7. The method of claim 6, wherein the first reference value is a minimum value from among average heart rates for multiple epochs in a series of intervals immediately preceding the particular epoch;
   wherein the second reference value is a minimum value from among average heart rates for multiple epochs in a series of epochs immediately preceding the particular epoch; and
   wherein the epoch-level relative heart rate measure for the particular epoch is an average of the first difference for the particular epoch and the second difference for the particular epoch.

8. The method of claim 1, wherein determining the approximate entropy measures comprises determining one or more approximate entropy factor scores that have a value within a predefined range and indicate a relationship of an approximate entropy distribution with respect to an approximate entropy reference value; and
   wherein determining the relative heart rate measures comprises determining one or more heart rate factor scores that have a value within a predefined range and indicate a relationship of a relative heart rate distribution with respect to a reference value.

9. The method of claim 8, wherein the predefined ranges for the one or more approximate entropy factor scores and the relative heart rate factor scores are a same predefined range; and
   wherein the approximate entropy factor scores and the relative heart rate factor scores are generated using a logistic function.

10. The method of claim 1, wherein determining the first score for a particular interval comprises determining a mean of (i) the relative heart rate measure for the particular interval and (ii) a first approximate entropy factor score indicating a relationship of approximate entropy values for the particular interval with respect to an average of approximate entropy values;
   wherein obtaining the sleep stage likelihood scores further comprises determining a third score indicating a likelihood that the particular portion of the time period represents a slow wave sleep stage as:
      a score derived using one or more HRV ratios for the particular interval; or
      a mean of (i) the score derived using one or more HRV ratios for the particular interval and (ii) a second approximate entropy factor score indicating a relationship of approximate entropy values with respect to a reference indicating a lowest percentage of approximate entropy values for the particular interval.

11. The method of claim 10, wherein the slow wave sleep score is the mean of the HRV ratio and the second approximate entropy factor score;
   wherein the second approximate entropy factor score is determined based on (i) a mean of approximate entropy values for the particular interval from a lowest approximate entropy value up to a particular percentile of the approximate entropy values and (ii) a mean of approximate entropy values for the particular interval from a lowest approximate entropy value up to a percentile of the approximate entropy values that is greater than the particular percentile.

12. The method of claim 1, wherein the sleep stage labels include labels corresponding to stages for wake, rapid eye movement (REM) sleep, light sleep, and deep or slow-wave sleep.

13. The method of claim 1, wherein assigning the sleep stage labels comprises:
   determining, for each of the intervals, (i) a likelihood that the interval corresponds to REM sleep, and (ii) an indication whether the interval is classified as REM sleep;
   determining, for each of the intervals, (i) a likelihood that the interval corresponds to light sleep, and (ii) an indication whether the interval is classified as light sleep;
   determining, for each of the intervals, (i) a likelihood that the interval corresponds to slow-wave sleep, and (ii) an indication whether the interval is classified as slow-wave sleep; or
   determining, for each of the intervals, (i) a likelihood that the interval corresponds to a wake stage, and (ii) an indication whether the interval is classified as a wake stage.

14. The method of claim 1, wherein the sensor data comprises at least one selected from a group consisting of: (i) EKG signal data from EKG sensor, and (ii) heartbeat data from a heartbeat sensor.

15. The method of claim 1, wherein dividing the time period into a series of intervals comprises diving the time period into adjacent periods each having a same duration.

16. The method of claim 1, wherein analyzing the heart rate of the person comprises evaluating the value of a heart rate signal in each interval with respect to the values in a neighborhood of the interval, wherein the neighborhood for each interval is a time window that extends from a first time threshold that precedes the interval to a second time threshold that follows the interval.

17. The method of claim 1, wherein the obtained sensor data corresponds to a sleep session of the person; and
   wherein analyzing the heart rate of the person comprises evaluating an absolute value of the heart rate signal with respect to the rest of the heart rate values for the sleep session and predetermined thresholds.

18. The method of claim 1, wherein assigning the sleep stage labels comprises assigning a sleep stage label to a particular portion of the time period, comprising:
   providing multiple signals that are separately correlated to sleep stages as input to a sleep stage classifier; and
   obtaining a single sleep stage label for the particular portion of the time period based on output of the sleep stage classifier.

19. The method of claim 1, comprising detecting heartbeats by:
   detecting peaks in an EKG signal;
   determining a derivative signal from of the EKG signal by determining, for each sample of the EKG signal, a difference of between a current sample and an immediately previous sample;
   identifying R waves based on applying one or more thresholds to the derivative signal; and
   detecting the heartbeats based on the identified R waves.

20. The method of claim 1, wherein analyzing the heart rate and the changes in the heart rate comprises determining, for each of the intervals, (i) multiple approximate entropy factors corresponding to mean values of different ranges of the determined approximate entropy scores, (ii) multiple HRV ratio factors corresponding to mean values of different ranges of the determined HRV ratios; and
   wherein obtaining sleep stage likelihood scores comprises determining, for each of the intervals, a probability of one or more sleep stages based on a combination of one of the approximate entropy factors for the interval and one of the HRV ratio factors for the interval.

21. The method of claim 1, wherein analyzing the heart rate and the changes in the heart rate comprises determining an additional heart rate measure for an interval computed as an exponential average the series of heart rate values for the interval minus a median of the series of heart rate values; and
   wherein the sleep stage likelihood scores are obtained based on the additional heart rate measure.

22. The method of claim 1, wherein generating the approximate entropy measures comprises:
   counting, for an interval, a number of incidences of sliding windows for which a maximum difference in corresponding elements is less than a comparison threshold; and
   averaging logarithmic sums of the counts.

23. The method of claim 1, comprising detecting heartbeats, comprising:
   identifying local maxima and local minima in an EKG signal;
   computing ranges between the maximum value of the EKG signal and minimum value of the EKG signal within each of multiple windows of the EKG signal; and
   assigning, to each of the multiple windows, a probability of the window representing a beat.

24. A system comprising:
one or more computing devices;
one or more computer-readable media storing instructions that, when executed by the one or more computing devices, cause the one or more computing devices to perform operations comprising:
   obtaining, by the one or more computing devices, sensor data generated by one or more sensors over a time period while a person is sleeping;
   dividing, by the one or more computing devices, the time period into a series of intervals;
   analyzing, by the one or more computing devices, heart rate and the changes in the heart rate of the person indicated by the sensor data over the intervals, wherein the analysis comprises:
      determining approximate entropy measures indicating approximate entropy of a heart rate of the person for each of the intervals, comprising determining a series of heart rate values corresponding to different times within each interval and assessing multiple sliding windows of the heart rate values within each interval;
      generating a heart-rate variability (HRV) signal for each of the intervals, performing a frequency analysis of the HRV signals, and generating HRV ratios each indicating a ratio of low frequency components of the HRV signal to high frequency components of the HRV signal; and
      determining a relative heart rate measure for each of the intervals, each relative heart rate measure being determined based on multiple different windows over a series of sub-interval epochs within the interval, wherein the relative heart rate measure for an interval is determined based on comparisons, for each particular epoch of at least some of the epochs, of a heart rate measure for the particular epoch with heart rate measures for epochs that occur before and after the particular epoch in the window corresponding to the particular epoch;
   obtaining sleep stage likelihood scores determined by multiple different sleep stage analysis functions based on the approximate entropy measures, the HRV ratios, and the relative heart rate measures, comprising:
      determining, based on one or more of the approximate entropy measures and one or more of the relative heart rate measures, a first score indicating a likelihood that the sleep stage for a particular portion of the time period is in a set consisting of a REM stage and a wake stage; and
      determining a second score to discriminate between the REM stage and the wake stage, the second score being determined based on (i) a measure representing a comparison of a measure of heart rate during the particular portion with a resting reference heart rate for the person and (ii) a level of movement of the person during the particular portion of the time period;
   assigning, by the one or more computing devices, sleep stage labels to different portions of the time period based on a combination of the likelihood scores from the multiple different sleep stage analysis functions; and providing, by the one or more computing devices, an indication of the assigned sleep stage labels.

25. One or more computer-readable media storing instructions that, when executed by one or more computing devices, cause the one or more computing devices to perform operations comprising:

obtaining, by the one or more computing devices, sensor data generated by one or more sensors over a time period while a person is sleeping;

dividing, by the one or more computing devices, the time period into a series of intervals;

analyzing, by the one or more computing devices, heart rate and the changes in the heart rate of the person indicated by the sensor data over the intervals, wherein the analysis comprises:

determining approximate entropy measures indicating approximate entropy of a heart rate of the person for each of the intervals, comprising determining a series of heart rate values corresponding to different times within each interval and assessing multiple sliding windows of the heart rate values within each interval;

generating a heart-rate variability (HRV) signal for each of the intervals, performing a frequency analysis of the HRV signals, and generating HRV ratios each indicating a ratio of low frequency components of the HRV signal to high frequency components of the HRV signal; and determining a relative heart rate measure for each of the intervals, each relative heart rate measure being determined based on multiple different windows over a series of sub-interval epochs within the interval, wherein the relative heart rate measure for an interval is determined based on comparisons, for each particular epoch of at least some of the epochs, of a heart rate measure for the particular epoch with heart rate measures for epochs that occur before and after the particular epoch in the window corresponding to the particular epoch;

obtaining sleep stage likelihood scores determined by multiple different sleep stage analysis functions based on the approximate entropy measures, the HRV ratios, and the relative heart rate measures, comprising:

determining, based on one or more of the approximate entropy measures and one or more of the relative heart rate measures, a first score indicating a likelihood that the sleep stage for a particular portion of the time period is in a set consisting of a REM stage and a wake stage; and determining a second score to discriminate between the REM stage and the wake stage, the second score being determined based on (i) a measure representing a comparison of a measure of heart rate during the particular portion with a resting reference heart rate for the person and (ii) a level of movement of the person during the particular portion of the time period;

assigning, by the one or more computing devices, sleep stage labels to different portions of the time period based on a combination of the likelihood scores from the multiple different sleep stage analysis functions; and providing, by the one or more computing devices, an indication of the assigned sleep stage labels.

* * * * *